United States Patent
Kimura et al.

(10) Patent No.: US 8,182,916 B2
(45) Date of Patent: May 22, 2012

(54) PARTICULATE WATER ABSORBING AGENT COMPRISING CROSSLINKED ABSORBENT RESIN AND HAVING LOW RESIDUAL MONOMER, WATER ABSORBING ARTICLE AND METHOD FOR PRODUCTION OF WATER ABSORBING AGENT

(75) Inventors: Kazuki Kimura, Toyooka (JP); Shin-ichi Fujino, Himeji (JP); Katsuyuki Wada, Himeji (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 899 days.

(21) Appl. No.: 11/816,200

(22) PCT Filed: Feb. 10, 2006

(86) PCT No.: PCT/JP2006/302782
§ 371 (c)(1),
(2), (4) Date: Oct. 3, 2008

(87) PCT Pub. No.: WO2006/088115
PCT Pub. Date: Aug. 24, 2006

(65) Prior Publication Data
US 2010/0062252 A1    Mar. 11, 2010

(30) Foreign Application Priority Data

Feb. 15, 2005  (JP) ................................ 2005-038123
Mar. 25, 2005  (JP) ................................ 2005-089307

(51) Int. Cl.
B32B 5/16 (2006.01)
C08F 2/10 (2006.01)
C08F 8/34 (2006.01)
C08J 3/24 (2006.01)

(52) U.S. Cl. ............... 428/403; 428/407; 525/327.4; 525/327.5; 525/329.7; 525/329.8; 526/89; 526/234; 526/317.1; 526/319

(58) Field of Classification Search ................. 428/403, 428/407; 525/327.4, 327.5, 329.7, 329.8; 526/89, 234, 317.1, 319
See application file for complete search history.

(56) References Cited

U.S. PATENT DOCUMENTS

| | | | |
|---|---|---|---|
| 5,229,488 A | | 7/1993 | Nagasuna et al. |
| 5,610,208 A * | | 3/1997 | Dairoku et al. ............... 525/384 |
| 5,866,678 A | | 2/1999 | Kajikawa et al. |
| 6,660,819 B2 * | | 12/2003 | Chmelir et al. ............... 526/217 |
| 6,720,389 B2 | | 4/2004 | Hatsuda et al. |
| 6,875,511 B2 * | | 4/2005 | Dairoku et al. ............... 428/402 |
| 6,906,159 B2 * | | 6/2005 | Dairoku et al. ............ 526/317.1 |
| 6,914,099 B2 * | | 7/2005 | Kim ............................... 525/343 |
| 7,183,456 B2 | | 2/2007 | Hatsuda et al. |
| 7,193,006 B2 | | 3/2007 | Ishizaki et al. |
| 7,196,139 B2 * | | 3/2007 | Fujimaru et al. ............... 525/218 |
| 7,250,459 B2 * | | 7/2007 | Dairoku et al. ............... 524/322 |
| 7,312,278 B2 * | | 12/2007 | Nakashima et al. .......... 525/119 |
| 7,378,453 B2 * | | 5/2008 | Nogi et al. ....................... 521/53 |
| 7,473,470 B2 * | | 1/2009 | Ishizaki et al. ................. 428/407 |
| 7,473,739 B2 * | | 1/2009 | Dairoku et al. ............ 525/327.6 |
| 2002/0061978 A1 | | 5/2002 | Hatsuda et al. |
| 2004/0110006 A1 | | 6/2004 | Ishizaki et al. |
| 2004/0181031 A1 | | 9/2004 | Nogi et al. |
| 2004/0186244 A1 | | 9/2004 | Hatsuda et al. |
| 2004/0254553 A1 * | | 12/2004 | Fujimaru et al. ............... 604/372 |
| 2006/0276598 A1 | | 12/2006 | Wada et al. |
| 2007/0149691 A1 | | 6/2007 | Ishizaki et al. |
| 2009/0036855 A1 * | | 2/2009 | Wada et al. .................... 604/372 |
| 2009/0318885 A1 * | | 12/2009 | Dairoku et al. ............... 604/367 |

FOREIGN PATENT DOCUMENTS

CN         1530384         9/2004
(Continued)

OTHER PUBLICATIONS

Tani No Jiten (dictionary of units), 4th Ed., Maruzen, 1996, p. 299-300.

*Primary Examiner* — Hoa (Holly) Le
(74) *Attorney, Agent, or Firm* — Roylance, Abrams, Berdo & Goodman, L.L.P.

(57) ABSTRACT

An object of the present invention is to provide a water absorbing agent having a low amount of residual monomer, small variance of the amount of residual monomer among ranges of particle size distribution and favorable absorption properties, and being sanitary; an absorbing article; and a method for the production of a water absorbing agent. The water absorbing agent of the present invention has the amount of residual monomer of not higher than 500 ppm, and a residual monomer index of not greater than 0.30. The method for the production includes a first step of obtaining a hydrogel polymer by polymerizing an aqueous solution of a monomer including an unsaturated carboxylic acid and/or a salt thereof in the presence of a crosslinking agent; a second step of obtaining a water absorbent resin precursor which is in powder form and includes particles having a particle size of 300 to 850 μm and particles having a particle size of smaller than 300 μm as main components by drying said hydrogel polymer followed by pulverization and classification to adjust the particle size distribution, a third step of obtaining a water absorbent resin by heating a mixture of said water absorbent resin precursor and a surface crosslinking agent, which can form an ester bond around the surface of said water absorbent resin precursor, a fourth step of adding by spraying an aqueous solution that includes a sulfur-containing reducing agent to said water absorbent resin, and a fifth step of subjecting the mixture of the water absorbent resin and said aqueous solution to a heat treatment under an airflow of not lower than 40° C. but not higher than 120° C.

13 Claims, No Drawings

FOREIGN PATENT DOCUMENTS

| | | |
|---|---|---|
| EP | 1462473 | 9/2004 |
| JP | 63-7203 | 2/1988 |
| JP | 4-106108 | 4/1992 |
| JP | 04120111 | 4/1992 |
| JP | 7-98847 | 10/1995 |
| JP | 2004-300425 | 10/2004 |
| JP | 2004-359943 | 12/2004 |
| WO | 91/03497 | 3/1991 |
| WO | 02/053605 | 7/2002 |
| WO | WO 2004/099265 | 11/2004 |

* cited by examiner

PARTICULATE WATER ABSORBING AGENT COMPRISING CROSSLINKED ABSORBENT RESIN AND HAVING LOW RESIDUAL MONOMER, WATER ABSORBING ARTICLE AND METHOD FOR PRODUCTION OF WATER ABSORBING AGENT

TECHNICAL FIELD

The present invention relates to a water absorbing agent, an absorbing article and a method for the production of a water absorbing agent.

BACKGROUND ART

In recent years, a water absorbing agent aiming at absorption of body fluids has been widely utilized in sanitary goods such as a disposable diaper, a sanitary napkin, an incontinence pad, and the like. As this water absorbing agent, for example, cross-linked polymers of partially neutralized polyacrylic acid and the like have been known, which have been generally used in particulate forms although those in the form of sheet-like, fibrous, film-like or the like have been also known.

Characteristics expected for this water absorbing agent include water-absorption properties, i.e., high absorption capacity without load and high absorption capacity under a load, of course. However, problems of sanitary aspects and odor must be also considered because it may be used in sanitary goods such as disposable diapers. In connection with causes that affect the problems of sanitary aspects and odor, they may result from the raw materials of the water absorbing agent. Among them, one known cause may be attributed to an unreacted monomer that remains in the water absorbing agent in a slight amount. Therefore, the amount of residual monomer being low in the water absorbing agent has been desired.

As techniques for reducing the amount of residual monomer in a water absorbent resin, (1) a process in which amount of a radical polymerization initiator added to a monomer liquid is increased by adding two times or more in divided fractions (JP-B No. S63-7203), (2) a process in which a radical polymerization initiator is added to a hydrogel polymer during or following polymerization (JP-A No. 2004-517179), and (3) a process in which a reductive substance is added to a hydrogel polymer prior to or during drying (JP-B No. H7-98847) were disclosed. Moreover, (4) a process in which a reductive substance is mixed in combination when a water absorbent resin is mixed with an aqueous surface crosslinking agent solution (JP-A No. H04-106108), and (5) a process in which a reductive substance is mixed when a water absorbent resin after completing a surface crosslinking treatment is mixed with a mixing activator such as a surfactant and water insoluble fine particles (pamphlet of International Publication No. 91/03497), and the like were also disclosed.

However, when the amount of residual monomer is reduced using the technique described in the above processes (1) and (2), the resulting water absorbent resin may be colored. Thus, the water absorbent resin has come to be seen through a top sheet of the absorbing article, leading to a problem of deterioration of the commercial value. Furthermore, because various severe conditions are required for reducing the amount of residual monomer, physical properties may be impaired due to deterioration of the polymer. Accordingly, there exists a problem of difficulty in achieving a balance between lowering of residual monomer to a desired level, and keeping or improvement of absorption properties such as absorption capacity without load, absorption capacity under a load and the like. In addition, also in the cases of the above processes (3) and (4), a problem of emission of a bad smell may be raised which is believed to be derived from a component generated upon the heat treatment in the following step through binding of the added reductive substance and impurities derived from the raw material, although detailed grounds are uncertain. Therefore, these processes are not suited for use in production of absorbing articles such as diapers. Moreover, also in the case of the above process (5), when the water absorbing agent was removed from an absorbing article such as a diaper followed by measuring the amount of residual monomer, problems of great variance of the amount of residual monomer of the water absorbing agent among the absorbing articles may be involved in which those having the amount of residual monomer which had not been reduced to a desired level, or those out of spec are found, although the amount of residual monomer is surely reduced. This may result in problems of odor and sanitary aspects, or provide products out of spec as the case may be, under current circumstances in which lowering in thickness of absorbing articles has been preferred, thereby decreasing the amount of pulp or the like of hydrophilic fibers that constitute this absorbing article, and in which further increasing the probability of contact of the water absorbing agent with skin of the user.

DISCLOSURE OF THE INVENTION

An object of the present invention is to provide a water absorbing agent having a low amount of residual monomer, small variance of the amount of residual monomer among ranges of particle size distribution and favorable absorption properties, and being sanitary; a method for production of the same, and an absorbing article.

The present inventor elaborately investigated in order to solve the problems described above. As a consequence, it was found that variance of the amount of residual monomer of the water absorbing agents among absorbing articles such as diapers results from the variance of particle size distribution of the water absorbing agent, and that because there are differences of the water absorbing agents in the amount of residual monomer among the ranges of particle size distribution, the amount of residual monomer varies depending on this variance of the particle size distribution. Moreover, it was revealed that a large amount of the residual monomer is found in particles having a small particle size among the particles of the water absorbing agent.

More specifically, when a powdery water absorbing agent is supplied to absorbing articles from the apparatus for producing the absorbing articles such as diapers, the water absorbing agent occurs particle segregation not a little. Thus, it was revealed that the amount of residual monomer of the water absorbing agent supplied to each one of the absorbing articles such as diapers varies, and at the same time, particle size distribution also varies. Furthermore, when each amount of residual monomer of each water absorbing agent was measured by its particle size, it was found that the amount of residual monomer is greatly different in each range of particle size distribution. More specifically, it was elucidated that although the amount of residual monomer did not vary so much when compared among the particles having the same particle size; for example, among the particles having a particle size of not smaller than 300 μm, but the amount of residual monomer of the particles having a particle size of not smaller than 300 μm was different from the amount of residual monomer of the particles having a particle size of smaller than 300 μm when the particles were taken from one diaper, suggesting difference between the ranges of particle size distribution. In other words, it was found that the amount of residual monomer of a water absorbing agent differs in each range of particle size distribution, elucidating that variance of the amount of residual monomer of the water absorbing agent taken from an absorbing article may result from differences generated in the amount of residual monomer among the ranges of particle size distribution which may be attributable to accompanying segregation.

Causes of the difference in the amount of residual monomer among the ranges of particle size distribution may be considered as follows. When the water absorbent resin is obtained by aqueous polymerization, the amount of residual monomer in the hydrogel polymer after completing polymerization is usually 50,000 to 100,000 ppm, however, the amount of residual monomer becomes several hundreds ppm when this polymer was dried. This event is caused because the polymerization initiator remaining in the hydrogel polymer particles acts on the residual monomer to permit polymerization under a high temperature provided by drying. In this stage, moisture content of the surface of the polymer gel and small gel particles which can be dried at high speed will be quickly declined, therefore, the residual initiator is inactivated, or probability of encounter of the monomer and the residual initiator is lowered due to the declined moisture content. Accordingly, polymerization of the residual monomer will be terminated. Therefore, the monomer remains in a large amount at parts that are easy to be dried, specifically, on the surface of the dried matter and small gel particles of the polymer gel. Also, monomer vapor which evaporated during drying may be adsorbed to the surface of other dried matter, which may also allow the monomer to be present in a large amount on the dried matter surface. Moreover, progress of polymerization of the residual monomer during drying may be disabled because the polymer after completing the polymerization is brought into contact with oxygen, thereby causing inactivation of the initiator radical on the gel surface and small gel particles through acting with oxygen in the air.

As in the foregoings, in the step of drying the hydrogel polymer, it is believed that the amount of residual monomer varies among the gel particles, thereby forming gradation also present in one particle in which the amount of residual monomer becomes greater at the closer point to the surface side.

Furthermore, when the dried matter of the hydrogel polymer is pulverized as needed, small particles are expected to be particles having a large amount of residual monomer because the pulverization usually occurs from the surface part that is likely to be disrupted and includes a large amount of residual monomer, although it may depend on the apparatus for pulverization.

When the water absorbent resin is obtained by reversed phase suspension polymerization, any pulverizing step is not generally incorporated in many cases, however, the difference in the amount of residual monomer on the basis of the variance of particle size distribution is caused. When water and the suspension solvent (cyclohexane, n-hexane or the like) are eliminated by distillation after completing the polymerization, a part of the residual monomer is eliminated through elution into the solvent. In this stage, differences in the residual monomer among the ranges of particle size distribution are caused. Even though the amount of residual monomer is constant depending on state of the gel, surface area per unit volume varies between fine particles and coarse particles. Because the amount eluted from inside of the gel is dependent on the surface area, the coarse particles are estimated to be more apt to include the residual monomer.

From the aspects described hereinabove, the present inventor introduced "index of residual monomer among ranges of particle size distribution (RMI: Residual Monomer Index)" calculated by the following formula (1) as a marker for regulating variance of the amount of residual monomer among the ranges of particle size distribution of the water absorbing agent, and thus, by regulating this residual monomer index to fall within a predetermined range, a water absorbing agent having a low amount of residual monomer and small variance of the amount of residual monomer among the ranges of particle size distribution and being sanitary was accomplished.

$$RMI = |RM_1 - RM_2| / RM_A \qquad (1)$$

wherein, $RM_1$ represents the amount of residual monomer of the water absorbing agent having a particle size of smaller than 300 μm among the particles constituting the water absorbing agent; $RM_2$ represents the amount of residual monomer of the water absorbing agent having a particle size of 300 to 850 μm among the particles constituting the water absorbing agent; and $RM_A$ represents the amount of residual monomer of the water absorbing agent. When $RM_A$ is 0, RMI should be 0. Also, $|RM_1 - RM_2|$ means an absolute value for $(RM_1 - RM_2)$.

The water absorbing agent according to the present invention is a particulate water absorbing agent comprising as a principal component a water absorbent resin which has a cross-linked structure including a constitutional unit derived from an unsaturated carboxylic acid and/or a salt thereof and which is obtained by a surface crosslinking treatment around the surface thereof with a surface crosslinking agent, said water absorbing agent comprising particles having a particle size of 300 to 850 μm and particles having a particle size of smaller than 300 μm, wherein the amount of residual monomer is not lower than 0 but not higher than 500 ppm, and residual monomer index (RMI) calculated by the above formula (1) is not greater than 0.30.

The absorbing article according to the present invention comprises the aforementioned water absorbing agent.

The method for the production of a water absorbing agent according to the present invention comprises:

(1) a step of obtaining a hydrogel polymer by polymerizing an aqueous solution of a monomer including an unsaturated carboxylic acid and/or a salt thereof in the presence of a crosslinking agent;

(2) a step of obtaining a water absorbent resin precursor which is in powder form and includes particles having a particle size of 300 to 850 μm and particles having a particle size of smaller than 300 μm as main components by drying said hydrogel polymer followed by pulverization and classification to adjust the particle size distribution, (3) a step of obtaining a water absorbent resin by heating a mixture of said water absorbent resin precursor and a surface crosslinking agent, which can form an ester bond around the surface of said water absorbent resin precursor, (4) a step of adding by spraying an aqueous solution that includes a sulfur-containing reducing agent to said water absorbent resin, and (5) a step of subjecting the mixture of the water absorbent resin and said aqueous solution to a heat treatment under an airflow of not lower than 40° C. but not higher than 120° C.

The water absorbing agent of the present invention has low amount of residual monomer and has small variance of the amount of residual monomer among the ranges of particle size distribution, therefore, when it is used in absorbing articles, variance of the amount of residual monomer among absorbing articles due to particle segregation becomes small. Thus, sanitary products may be provided even though it is used in absorbing articles of slim type which have been in widespread use in recent years.

As described above, the present inventor found that the residual monomer of a water absorbing agent is not present homogenously on/in the water absorbing agent particles, but particularly in water absorbing agents obtained by aqueous polymerization, it may be present in a larger amount on the surface part and in fine particles, also with respect to the water absorbing agent particles. According to conventional methods for reducing the residual monomer, because the residual monomer was believed to be present homogenously also inside of the particle, excessive treatment for reducing the residual monomer has been carried out toward the inside and whole of the particles in order to treat the residual monomer of the water absorbing agent as a whole (inside of the particles, large particles). Thus, various physical properties of the water absorbing agent were deteriorated. As a consequence, it was difficult to achieve a balance between lowering of the amount of residual monomer, and favorable physical properties such as e.g., high absorption capacity under a load, suppression of coloring and the like. However, according to the method for production of the present invention, the residual monomer on/in the surface and fine particles of the water absorbing agent particles is selectively treated, therefore, a balance between lowering of the residual monomer and favorable physical properties can be achieved.

With respect to the water absorbing agent of the present invention, the method for production of the same is not particularly limited. In the present invention, as the means for selectively treating the residual monomer on/in the surface and fine particles of the water absorbing agent particles, for example, the method for production of the present invention (surface crosslinking treatment, followed by adding an aqueous solution including a small amount of a sulfur-containing reducing agent, and further subjecting to an additional heat treatment under a predetermined condition) may be employed, or a method for production disclosed in Japanese Patent Application No. 2005-038123 may be also employed under selected conditions. According to the method for production of the present invention, surface crosslinking enables homogenous addition by spraying of a small amount of the aforementioned aqueous solution. In addition, according to the method for production of the present invention in which just a small amount of the aqueous solution is used, the aqueous solution is preferentially incorporated by the surface and the fine particles, leading to selective and preferential treatment of the residual monomer on/in the surface and the fine particles of the water absorbing agent particles by a heat treatment (drying) under a predetermined airflow.

As in the foregoings, according to the method for the production of the water absorbing agent of the present invention, the aqueous solution that includes a sulfur-containing reducing agent is homogeneously mixed with the water absorbent resin by spraying, and subjected to a heat treatment. Therefore, also in the case of the water absorbent resin having varying amount of residual monomer depending on the difference in the range of particle size distribution, the sulfur-containing reducing agent efficiently acts on the residual monomer, and thus, a water absorbing agent having low amount of residual monomer, and small variance of the amount of residual monomer among the ranges of particle size distribution can be obtained. Thus resulting water absorbing agent is not colored, does not give off any bad smell, and has favorable physical properties, without causing problems of impairment of physical properties, particularly absorption properties under a load, due to deterioration of the polymer.

Because the absorbing article of the present invention comprises a water absorbing agent having low amount of residual monomer and small variance of the amount of residual monomer among the ranges of particle size distribution, sanitary products can be provided which are not colored, without need of concern of variance of the amount of residual monomer due to particle segregation, and occurrence of out of spec products.

BEST MODE FOR CARRYING OUT THE INVENTION

Hereinafter, the water absorbing agent, the absorbing article and the method for the production of a water absorbing agent according to the present invention will be explained in detail according to the preferred embodiments, however, scope of the present invention is not bound by these descriptions. In addition to the following exemplifications, alteration can be made ad libitum without departing from the scope and principles of the present invention.

The first step in the method for the production of a water absorbing agent according to the present invention is a step for generating a hydrogel polymer (hereinafter, may be also referred to as polymer gel) by allowing a monomer including an unsaturated carboxylic acid and/or a salt thereof to be polymerized. The unsaturated carboxylic acid is not particularly limited as long as it has 1 or more carboxyl groups in one molecule, but examples thereof include acrylic acid, methacrylic acid, maleic acid, itaconic acid, cinnamic acid, crotonic acid and the like. In light of performances and cost of the resulting water absorbing agent, acrylic acid and/or a salt thereof is preferably included as a main component. When acrylic acid and/or a salt thereof is included as a main component, i.e., when a polyacrylic acid (partially neutralized) cross-linked polymer is included as a main component, in addition to the aforementioned unsaturated carboxylic acid, a monomer may be used in combination as needed. Examples of such a monomer include: anionic unsaturated monomers such as maleic anhydride, vinyl sulfonic acid, allyl toluenesulfonic acid, vinyl toluenesulfonic acid, styrenesulfonic acid, 2-(meth)acrylamide-2-methylpropanesulfonic acid, 2-(meth)acryloylethanesulfonic acid, 2-(meth)acryloylpropanesulfonic acid and 2-hydroxyethyl(meth)acryloyl phosphate, and salts thereof; mercapto group-containing unsaturated monomers; phenolic hydroxyl group-containing unsaturated monomers; amide group-containing unsaturated monomers such as (meth)acrylamide, N-ethyl(meth)acrylamide and N,N-dimethyl(meth)acrylamide; amino group-containing unsaturated monomers such as N,N-dimethylaminoethyl(meth)acrylate, N,N-dimethylaminopropyl(meth)acrylate and N,N-dimethylaminopropyl(meth)acrylamide; and the like. These monomers may be used alone together with the aforementioned unsaturated carboxylic acid and/or a salt thereof, or two or more these monomers may be used as a mixture ad libitum.

Examples of the salt of the unsaturated carboxylic acid including acrylic acid include salts of sodium, lithium, potassium, ammonium, amine and the like. Among them, sodium salt is preferred in light of costs. Using amount of acrylic acid and/or a salt thereof is preferably not lower than 70% by mole, more preferably not lower than 80% by mole, still more preferably not lower than 90% by mole, and particularly preferably not lower than 95% by mole per the entire monomer component (except for the internal crosslinking agent described later). The upper limit is 100% by mole. When the monomer is an acid group-containing monomer including acrylic acid, its neutralization ratio is not particularly limited, and the neutralization may be performed following the neutralization as needed. For applications such as in sanitary goods which may be brought into contact with a human body, also taking into consideration of unnecessity of neutralization following the polymerization, the neutralization ratio may be preferably not less than 40% by mole but not greater than 90% by mole, and more preferably the lower limit being 50% by mole and the upper limit being 80% by mole.

The polymerization may be carried out by aqueous polymerization or reversed phase suspension polymerization. Although the concentration of the aqueous monomer solution is not particularly limited, but is preferably not lower than 10% by weight but not higher than 70% by weight, and particularly preferably not lower than 20% by weight but not higher than 60% by weight. Moreover, when the aqueous polymerization or reversed phase suspension polymerization is carried out, a solvent other than water can be also used in combination. Further, type of the solvent is not particularly limited. The concentration of the aqueous monomer solution is also a preferable solid content of a hydrogel polymer referred to herein. The solid content of the hydrogel polymer may be determined based on a dried residue yielded after drying at 180° C. for 6 hours.

The polymerization can be carried out using a radical polymerization initiator. This radical polymerization initiator is not particularly limited, but one, or two or more may be selected and used ad libitum among those which have been utilized in production of common water absorbing agents depending on the type of the monomer to be polymerized and polymerization conditions. Examples of the same include thermal initiators such as e.g., persulfate salts such as sodium persulfate, potassium persulfate and ammonium persulfate; peroxides such as hydrogen peroxide, t-butyl peroxide and methylethylketone peroxide; azo compounds such as azonitrile compounds, azoamidine compounds, cyclic azoamidine compounds, azoamide compounds, alkylazo compounds, 2,2'-azobis(2-amidinopropane)dihydrochloride and 2,2'-azobis[2-(2-imidazoline-2-yl)propane]dihydroch bride; and the like, as well as photolytic initiators such as e.g., benzoin derivatives, benzyl derivatives, acetophenone derivatives, benzophenone derivatives, azo compounds and the like. In light of the cost performances and effect to reduce the residual monomer, thermal initiators are preferred, and persulfate salts are particularly preferred.

Also, a redox initiator may be prepared through combining with a reducing agent that accelerates decomposition of the aforementioned radical polymerization initiator. Examples of the reducing agent include (bi)sulfurous acid (sulfite) such as sodium sulfite and sodium bisulfite, L-ascorbic acid (ascorbate), reducing metals (salts) such as ferrous salt, amines, and the like. More preferably, the photolytic initiator and the thermal initiator are used in combination. Using amount of the radical polymerization initiator in this polymerization step is preferably not lower than 0.001 parts by weight but not higher than 2 parts by weight, and particularly preferably the lower limit being 0.01 parts by weight and the upper limit being 0.05 parts by weight per 100 parts by weight of the monomer. The using amount of the radical polymerization initiator being lower than 0.001 parts by weight is not preferred because the quantity of unreacted monomer may be so great that the amount of residual monomer in the resulting water absorbing agent is increased. In contrast, the using amount thereof beyond 2 parts by weight is not preferred because water-absorption properties, particularly absorption capacity under a load of the resulting water absorbing agent may be impaired. In addition, it is not preferred because a problem of the resulting water absorbing agent to be apt to be colored may be also raised. In the present invention, the residual monomer can be reduced under particular mild conditions for the treatment, therefore, impairment of the physical properties due to lowering of the residual monomer under conventional severe polymerization conditions and drying conditions can be avoided. In the polymerization step, instead of using the radical polymerization initiator, the polymerization reaction may be carried out through irradiating an active energy ray such as a radiation ray, an electron ray, an ultraviolet ray or the like to the reaction system.

In the polymerization step, a self-crosslinking type crosslinked polymer, or a cross-linked polymer in which a crosslinkable monomer such as an internal crosslinking agent as needed is formed, because the water absorbing agent of the present invention has a cross-linked structure derived from an unsaturated carboxylic acid and/or a salt thereof. As the internal crosslinking agent, any of known internal crosslinking agents having two or more polymerizable unsaturated groups in one molecule, or two or more reactive groups in one molecule can be used. Specific examples thereof include e.g., N,N'-methylenebis(meth)acrylamide, (poly)ethylene glycol di(meth)acrylate, (poly)propylene glycol di(meth)acrylate, trimethylolpropane tri(meth)acrylate, glycerin tri(meth)acrylate, glycerin acrylate methacrylate, ethylene oxide modified trimethylolpropane tri(meth)acrylate, pentaerythritol hexa (meth)acrylate, triallyl cyanurate, triallyl isocyanurate, triallyl phosphate, triallylamine, polyallyloxyalkane, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, glycidyl (meth)acrylate and the like. One, or two or more may be used among these. The cross-linked structure by the crosslinkable monomer such as an internal crosslinking agent may be formed through polymerization after adding to the monomer once in bulk, or through adding in divided fractions. Alternatively, it may be formed through adding to the hydrogel polymer following polymerization and allowing for crosslinking later.

Moreover, the water absorbent resin of the present invention is not limited to those which can be produced by the method for production disclosed herein, but any cross-linked polymer including the constitutional unit derived from the aforementioned monomer is permitted. The constitutional unit derived from the aforementioned monomer corresponds to a structure yielded by opening the polymerizable double bond of each monomer (structure yielded from double bond (C═C) turned to single bond (—C—C—)) by a polymerization reaction, for example.

Using amount of the internal crosslinking agent may be determined ad libitum depending on the characteristic of the desired water absorbing agent, however, in general, it is preferably not lower than 0.001 moles but not higher than 5 moles per 100 moles of the monomer. When the using amount of the internal crosslinking agent is lower than 0.001 moles, the gel strength may be lowered and the extractables may be increased. In contrast, when the using amount is higher than 5 moles, the absorption capacity tends to be lowered. The internal crosslinking agent may be added to the reaction system once in bulk, or in divided fractions. In the polymerization step, any of various foaming agents such as carbonate (hydrogen) salts, carbon dioxide, azo compounds and inert organic solvents (for example, 0 to 30 parts by weight per 100 parts by weight of the monomer); a hydrophilic polymer such as starch·cellulose, a derivative of starch·cellulose, polyvinyl alcohol, polyacrylic acid (polyacrylate) or polyacrylic acid (polyacrylate) cross-linked polymer (for example, 0 to 30 parts by weight per 100 parts by weight of the monomer); any of various surfactants; a chain transfer agent such as hypophosphorous acid (hypophosphite) (for example, 0 to 1 part by weight per 100 parts by weight of the monomer); may be added to the reaction system as needed.

Although the polymerization temperature is not particularly limited, but may be preferably not lower than 10° C. but not higher than 140° C., in general. When the polymerization temperature is lower than 10° C., the polymerization time becomes so long that productivity may be reduced, and also, the physical properties of the water absorbent resin may be deteriorated. In contrast, when the polymerization temperature is beyond 140° C., the physical properties of the water absorbent resin may be likewise deteriorated. Also, the polymerization time is not particularly limited, but may be determined ad libitum depending on type of the monomer and the polymerization initiator, as well as the polymerization temperature, and the like. Moreover, the polymerization may be usually carried out under an ordinary pressure in light of the apparatus, ease of operation and the like, however, it may be also carried out under a reduced pressure for the purpose of lowering the boiling temperature of the polymerization system.

The hydrogel polymer obtained by the polymerization has a solid content derived from the concentration of the aforementioned aqueous monomer solution, e.g., not lower than 10% by weight but not higher than 70% by weight, and is dried, pulverized and classified as needed to give a water absorbent resin precursor (second step). The hydrogel polymer is preferably subjected to the second step in the state of particulate forms of approximately 0.1 to 5 mm. The method for drying is not particularly limited, but any method in which a common dryer and a heating oven are used can be adopted. It is preferred that the drying temperature is not lower than 100° C. but not higher than 250° C. The lower limit may be preferably 120° C., and particularly preferably 150° C., while the upper limit may be preferably 220° C., and particularly preferably 200° C. The drying time is not particularly limited, which may be determined to be a time period such that the resultant dried matter has a desired solid content, for example, not lower than 80% by weight, preferably 85 to 100% by weight, and more preferably 90 to 100% by weight. It is preferred that drying is conducted such that the dried matter obtained by drying has a solid content, which is specified by dividing the weight of the dried residue yielded through heating at 180° C. for 3 hrs by the weight before drying, of not lower than 90% by weight, in light of ease of pulverization. In general, the drying may be carried out usually within 2 hours in light of the production efficiency although it may vary depending on the particle size of the polymer gel, the drying temperature, airflow which may be employed and the like.

The dried polymer is pulverized as needed. Although the pulverization may be generally carried out on the dried matter of the gelatinous polymer obtained in the drying step, it may be also carried out on the polymer before drying. The pulverization is preferably carried out so that more particles having a desired particle size can be obtained, and more preferably carried out through selecting pulverizing conditions ad libitum which can yield more particles having a particle size of 150 to 850 μm. Method for pulverization is not particularly limited, but any conventionally known method can be adopted.

The particle size distribution may be adjusted by dispersion polymerization and dispersion drying in the particulate forms, as in reversed phase suspension polymerization. However, in general, particularly in the case of aqueous polymerization, pulverization and classification may be carried out after drying to adjust to have a predetermined particle size distribution. The pulverized matter obtained in the pulverizing step is classified as needed to give the mass median particle size (D50) of particles of usually not smaller than 200 μm but not larger than 850 μm, thereby adjusting to have preferably a predetermined particle size distribution as powder. As the method for classification, any conventionally known method can be adopted.

In order to obtain the water absorbing agent of the present invention, with respect to the particle size of the pulverized matter as adjusted, mass median particle size (D50) may be limited to fall within a narrow range of usually 200 to 850 μm, preferably 200 to 710 μm, more preferably 250 to 600 μm, and particularly preferably 300 to 500 μm. In addition, content of the particles of smaller than 150 μm may be controlled to be 0 to 5% by weight, preferably 0 to 3% by weight, more preferably 0 to 2% by weight, and particularly preferably 0 to 1% by weight. Also, the aforementioned pulverized matter may have a weight ratio of particles having a particle size of 300 to 850 μm to particles having a particle size of smaller than 300 μm of not less than 5/95 but not greater than 95/5. Moreover, it is preferred that particles having a particle size of not smaller than 150 μm but not larger than 600 μm are controlled to account for not less than 90% by weight, still more not less than 95% by weight, and particularly not less than 98% by weight in the entire pulverized matter.

For example, for adjusting to give a predetermined particle size distribution in which the amount of fine particles of smaller than 150 μm is lessened while controlling the mass median particle size (D50) to fall within a narrow range of 250 to 600 μm, coarse particles and fine particles are removed as needed after the pulverization with a common apparatus for classification such as a mesh sieve. The coarse particles removed in this procedure may be preferably particles having a particle size of 600 to 5000 μm, and more preferably particles having a particle size of 850 to 2000 μm. Furthermore, the fine particles removed in adjusting the particle size distribution may be preferably particles having a particle size of smaller than 150 μm, and more preferably particles having a particle size of smaller than 200 μm. Thus removed coarse particles may be discarded as they are, but in general, they may be subjected to the pulverizing step as described above again.

Also, the removed fine particles may be discarded as they are, however, a step of regeneration to give larger particles or agglomerates in particulate form to enable use as the water absorbent resin of the present invention may be added. Any of steps disclosed in U.S. Pat. Nos. 6,228,930, 5,264,495, 4,950,692, 5,478,879 and European Patent No. 844270, Japanese Patent Application No. 2005-38123 and the like may be employed.

In particular, according to the technique disclosed in Japanese Patent Application No. 2005-38123, in the step of recovering fine particles containing a large amount of residual monomer as described above, the fine particles are recovered after reducing the amount of residual monomer. This technique is preferred as one of the methods for production to obtain the water absorbing agent of the present invention.

In the method for production disclosed in Japanese Patent Application No. 2005-38123, a radical polymerization initiator is not added to a polymer gel, but a thermal initiator (thermally decomposable radical polymerization initiator) is added to agglomerated particle side obtained from fine powder generated in the step of producing the water absorbent resin, followed by drying while allowing thus resulting agglomerated particles and polymer gel to coexist. According to this method for production, in comparison with the case in which a thermal initiator is directly added to the polymer gel, addition in the same amount (per unit weight of finally obtained water absorbent resin) enables the residual monomer to be reduced more effectively. Also, such an effect can be similarly achieved when an oxidizing agent or a reducing agent is used in place of the thermal initiator.

More specifically, the method for the production of a water absorbent resin disclosed in Japanese Patent Application No. 2005-38123 comprises obtaining a polymer gel having a water absorbing property; obtaining an agglomerated gel by adding an aqueous fluid containing at least one additive selected from the group consisting of thermal initiators, oxidizing agents and reducing agents to the fine powder which is obtained in the production of a water absorbent resin and has a mass median particle size falling within the range of 10 to 150 μm; and drying while allowing the agglomerated gel and the polymer gel to coexist.

According to the invention disclosed in Japanese Patent Application No. 2005-38123, a balance between lowering of the fine powder generated during the production step, and lowering of the amount of residual monomer in the resulting water absorbent resin can be achieved. More particularly, according to this invention, a water absorbent resin which includes a small amount of residual monomer and has a favorable physical property can be obtained while effectively reutilizing the fine powder generated in the production step of the water absorbent resin, without increasing using amount of an additive for reducing the residual monomer (at least one selected from the group consisting of thermal initiators, oxidizing agents and reducing agents). In other words, this method for the production of a water absorbent resin is a method in which the residual monomer can be efficiently reduced, and in addition, a beneficial effect in terms of the production costs, i.e., recycling of the fine powder, can be also achieved similarly to conventional recycling methods of fine powder through agglomeration. Therefore, the method for production disclosed in Japanese Patent Application No. 2005-38123 is preferred as an example of the method for the production of a water absorbing agent according to the present invention.

Hereinbelow, as an example of the method for the production of a water absorbing agent according to the present invention, the method for production disclosed in Japanese Patent Application No. 2005-38123 will be explained in detail. However, this method for production is not restricted by the following description, but in addition to the exemplifications below, alteration can be made ad libitum without departing from the principles of this method for production.

This method for production comprises a step of obtaining a polymer gel having a water absorbing property (hereinafter, may be also referred to as "polymerization step"). The following steps are not limited, but in general, a step of drying the polymer gel (hereinafter, may be also referred to as "drying step"), and a step of pulverizing the dried matter of the polymer gel (hereinafter, may be also referred to as "pulverizing step"), and a step of classifying the pulverized matter (hereinafter, may be also referred to as "classification step) may be further included. Particularly, this method for production can be referred to as being a method suited for continuously producing a water absorbent resin in which a water absorbent resin with lower amount of residual monomer can be obtained through reutilizing the fine powder obtained in the production of a water absorbent resin (for example, fine powder removed as a waste material in the aforementioned classification step and the like).

More specifically, in this method for production, it is important to add an aqueous fluid containing at least one additive selected from the group consisting of thermal initiators, oxidizing agents and reducing agents (hereinafter, may be also referred to as "essential additive") to the fine powder which is obtained in the production of a water absorbent resin and has a mass median particle size falling within the range of 10 to 150 thereby obtaining an agglomerated gel (hereinafter, may be also referred to as "agglomerated gel" or "agglomerated particle"), and to dry the agglomerated gel and the polymer gel while allowing them to coexist. In other words, the agglomerated particles obtained by mixing the fine powder and the aqueous fluid are subjected to a drying step together with the polymer gel obtained in the polymerization step.

The aforementioned agglomerated particle referred to in this method for production may be particles that include multiple fine powders, and has a median particle size of the agglomerated particle being not larger than 20 mm, preferably 0.3 to 10 mm, and more preferably 0.35 to 5 mm. Therefore, when a great mass of integrated gel is obtained by mixing the fine powder and the aqueous fluid, further drying and pulverization will be necessary.

The aforementioned agglomerated particle has a moisture content of preferably not higher than 75% by weight, more preferably not higher than 70% by weight, and still more preferably not higher than 65% by weight in light of the load in drying (the lower limit being beyond 0% by weight, and preferably not less than 5% by weight). When the moisture content of the agglomerated particle becomes excessively higher than that of the polymer gel, partially incomplete drying may be occurred in drying with the polymer gel. According to the findings acquired by the inventor of this method for production, when the agglomerated particles having a low moisture content are dried together with the polymer gel in the prior arts, the amount of residual monomer of the resulting water absorbent resin tends to be more markedly increased, therefore, it was necessary to keep the moisture content of the agglomerated particle high, in light of the residual monomer even though a load may be posed in the following drying step. However, according to this method for production, the residual monomer can be reduced enough even though the moisture content is comparatively lowered, and applications of this method for production may be significant when the moisture content falls within the aforementioned range.

The fine powder has a particle size that is smaller than the particle size of the water absorbent resin to be obtained by this method for production, and has been conventionally treated as a waste material, in general, as described above. Generally, it is preferred that the water absorbent resin has a mass median particle size (D50) (specified by JIS standard sieve classification) of 200 to 800 μm, and for example, the water absorbent resin obtained by this method for production preferably has a mass median particle size (D50) is from 200 to 450 μm. The fine powder is a residual matter yielded by excluding so that the resulting water absorbent resin has a mass median particle size (D50) falling within the desired range described above, and specifically, the mass median particle size (D50) falls within the range of 10 to 150 as described above. It is desired that the particles having a particle size of substantially smaller than 150 μm (specified by JIS standard sieve classification) are included in an amount of preferably 70 to 100% by weight, and still preferably 90 to 100% by weight. In addition, it is more preferred that the shape of the fine powder is irregular obtained by aqueous polymerization than spherical obtained by reversed phase suspension polymerization, in light of the strength of agglomeration. Moreover, the fine powder may or may not be one subjected to a surface crosslinking treatment which has been generally performed in production of water absorbent resins, or alternatively, any mixture thereof is also permitted.

All fine powder obtained by the production of a water absorbent resin can be subjected to the aforementioned agglomeration. In general, the fine powder obtained in the classification step may be predominantly used, however, not only the fine powder obtained in the classification step but, for example, the fine powder excluded by a bag filter or the like in the production step may be used in the agglomeration. Otherwise, fine powder obtained in a different step, or fine powder obtained in a separate production process (other production apparatus) can be also mixed and used. Furthermore, the fine powder may have the same composition as that of the polymer gel to be dried together, or may have a different composition. However, preferably, the fine powder having the same composition as that derived from the polymer gel to be dried together may be used.

In light of the mixing performance with the aqueous fluid and drying efficiency, the temperature of the fine powder is preferably not lower than 35° C., more preferably 40 to 100° C., and yet more preferably 45 to 80° C. The temperature of the fine powder may be adjusted ad libitum by incubating, heating, cooling or the like in each step of the production of the water absorbent resin.

The aqueous fluid which may be used in agglomerating the fine powder is prepared by dissolving the aforementioned essential additives in a solvent. The solvent is not particularly limited, but examples thereof include e.g., water, aqueous solutions including a hydrophilic organic solvent (for example, lower alcohols such as methyl alcohol, ethyl alcohol, n-propyl alcohol, isopropyl alcohol, n-butyl alcohol, isobutyl alcohol and t-butyl alcohol; ketones such as acetone; ethers such as dioxane and tetrahydrofuran; amides such as N,N-dimethylformamide; sulfoxides such as dimethylsulfoxide, and the like), and the like. In light of the physical properties and strength of agglomeration, the solvent includes water in the range of preferably 90 to 100% by weight, more preferably 99 to 100% by weight, and the solvent including water alone is particularly preferred. Moreover, in the aqueous fluid may be also included a small amount of other additive such as a crosslinking agent, a chelating agent, a surfactant and the like in the range not to impair the advantages of this method for production. For example, as the crosslinking agent, any type of the surface crosslinking agent described later may be used. By including the crosslinking agent in the aqueous fluid, lowering of the water soluble components and improvement of the strength of agglomeration can be expected.

Although the thermal initiator which may be used as the essential additive included in the aqueous fluid is not particularly limited as long as it can be decomposed to react with the monomer when the agglomerated particles and the polymer gel are allowed to coexist and dried, but examples thereof include e.g., potassium persulfate, ammonium persulfate, sodium persulfate, t-butylhydroperoxide, hydrogen peroxide, 2,2'-azobis(2-amidinopropane) dihydrochloride and the like. Among these, peroxide is preferred, and a persulfate salt such as sodium persulfate is particularly preferred. These thermal initiators may be used alone, or two or more thereof may be also used.

Although the oxidizing agent which may be used as the essential additive included in the aqueous fluid is not particularly limited as long as it can react with the monomer when the agglomerated particles and the polymer gel are allowed to coexist and dried, but examples thereof include e.g., inorganic oxidizing agents such as chlorate, bromate, chlorite and inorganic peroxides or organic peroxides illustrated also as the aforementioned thermal initiator such as hypochlorite, persulfate salts and hydrogen peroxide as well as t-butyl peroxide and benzoyl peroxide, and the like. Among these, persulfate salts and hydrogen peroxide are preferred, and persulfate salts are particularly preferred. These oxidizing agents may be used alone, or two or more thereof may be also used.

Although the reducing agent which may be used as the essential additive included in the aqueous fluid is not particularly limited as long as it can react with the monomer when the agglomerated particles and the polymer gel are allowed to coexist and dried, which may be either an organic reducing agent or an inorganic reducing agent, but may be preferably an inorganic reducing agent, and in particular, a sulfur-based, phosphorus-based, or nitrogen-based reducing agent is suitable. Specific, examples include e.g., sulfite (for example, sodium sulfite, potassium sulfite, ammonium sulfite and the like), bisulfite (for example, sodium bisulfite, potassium bisulfite, ammonium bisulfite and the like), pyrosulfite, dithionite, trithionate, tetrathionate, thiosulfate, nitrite, dimethylsulfoxide, thiourea dioxide, phosphite, nitrogen-containing organic compounds such as amino acids and ethanolamine, and the like. Among these, sulfur-based reducing agents, in particular, sulfite, bisulfite, pyrosulfite and dithionite are preferred. Preferable examples of the salt thereof include sodium salts, potassium salts and ammonium salts. Among all, sodium sulfite and sodium bisulfite are particularly preferred. These reducing agents may be used alone, or two or more thereof may be also used.

As the essential additive, a thermal initiator is preferred among those described above, and in particular, use of a persulfate salt as being essential one is preferred in light of possible achievement of excellent effect of reducing the residual monomer.

Content of the essential additive in the aqueous fluid is not particularly limited, but is preferably 0.0001 to 1% by weight per the fine powder, in general. When the content is lower than 0.0001% by weight, the residual monomer may not be reduced enough, while in contrast, when it is beyond 1% by weight, coloring of finally resulting water absorbent resin after drying may be caused.

In addition, the essential additive (particularly, thermal initiator) may be used in the polymerization step, as the case may be. In such instance, with respect to the content of the essential additive in the aqueous fluid, in general, the amount per unit weight of the fine powder before the agglomeration is preferably 1 to 500% by weight, more preferably 5 to 400% by weight, and still more preferably 10 to 300% by weight of the amount of the essential additive added in the polymerization step (amount per unit weight of the monomer component). When the proportion of the essential additive included in the aqueous fluid per the essential additive added in the polymerization step is out of the above range, the advantage of this method for production may not be accomplished. In the cases as described above (i.e., when the essential additive is used in the polymerization step), the essential additive added in the polymerization step and the essential additive included in the aqueous fluid may be the same type or the different type.

Characteristic of this method for production is to include the essential additive in the aqueous fluid. Although the effect in terms of the adding amount may be low in comparison with this case, the essential additive (particularly, thermal initiator)

may be added separately in an arbitrary step of this method for production apart from the addition to the aqueous fluid, for example, addition to the polymer gel before subjecting to the drying step, addition to the dried matter (dried polymer gel) before subjecting to the pulverizing step, or the like.

Using amount of the aqueous fluid is not particularly limited, but may be preferably not lower than 25 parts by weight but not higher than 280 parts by weight per 100 parts by weight of the fine powder. This using amount may be more preferably not higher than 200 parts by weight, and still more preferably not higher than 150 parts by weight. When the using amount of the aqueous fluid is beyond 280 parts by weight, great mass of integrated gel may be obtained, which may lead to necessity of further drying and pulverizing the gelatinous matter to give the agglomerated particles, and to need of an enormous load for the drying. In contrast, when the using amount of the aqueous fluid is lower than 25 parts by weight, strength of agglomeration may be insufficient, thereby possibly disabling excellent characteristics of the final product, accompanied by difficulties in agglomeration due to heterogeneous mixing.

Although mixing of the fine powder and the aqueous fluid may be merely executed upon agglomeration of the fine powder, however, in particular, it is preferred that the aqueous fluid is previously heated upon the agglomeration. Still more, according to a preferred embodiment, the heated aqueous fluid and the fine powder are mixed at a high speed, thereby permitting agglomeration. Hence, not great mass of integrated gel, but agglomerated particles of which size was directly controlled can be obtained. As a consequence, further drying and pulverizing the gelatinous matter to give agglomerated particles may not be required, and in addition, problems can be avoided that are caused in obtaining the great mass of integrated gel, i.e., problems of deterioration of the water absorbent resin itself due to cleavage, entanglement or the like of the main chain can be avoided, which may result from a huge force required in mixing, or from a kneaded state of a gelatinous block being formed.

In preferred embodiments of the agglomeration, the temperature of the aqueous fluid upon heating may be usually not lower than 40° C., preferably not lower than 50° C., and more preferably not lower than 60° C., and still more preferably not lower than 70° C. Moreover, the upper limit of the temperature may be not lower than the boiling point of the aqueous fluid, and the boiling point may be adjusted diversely by alteration of addition of a salt or other solvent, pressure (decompression, compression) and the like. However, great alteration is not caused even though the temperature is higher than 100° C., therefore, the temperature of not higher than 100° C. may be usually employed. When the aqueous fluid is previously heated, it is preferred that the essential additive is separately prepared to give an aqueous solution having a comparatively high concentration at room temperature or under cooling, and then mixed with the remaining aqueous fluid in a comparatively large amount which had been heated, immediately before mixing with the fine powder.

In preferred embodiments of the agglomeration, it is preferred that the fine powder itself is also heated in addition to previously heating the aqueous fluid. The temperature of the fine powder upon heating is also not lower than 40° C., and preferably not lower than 50° C., in general. Because great alteration is not caused even though the temperature is higher than 100° C., the temperature of not higher than 100° C. may be usually employed. When the fine powder itself is previously heated, the procedure is not particularly limited, but for example, the heating may be executed through incubation after heating by drying, or through heating externally in a separate manner.

In preferred embodiments of the agglomeration, upon mixing at a high speed of the heated aqueous fluid and the fine powder, mixing at a high speed means that time period required for completing mixing of the aqueous fluid and the fine powder to produce agglomerated particles is short. More specifically, time period starting from the time point at which the aqueous fluid is brought into contact with the fine powder until the time point at which the agglomerated particles are produced, i.e., mixing time, is short. The mixing time is preferably not longer than 3 min, more preferably not longer than 1 min, and most preferably from 1 sec to 60 sec. When the mixing time is long, homogenous mixing of the aqueous fluid and the fine powder may become difficult, and a great mass of integrated gel is liable to be formed. Furthermore, when the mixing time is too long, the essential additive included in the aqueous fluid may be decomposed before subjecting the generated agglomerated particles to the drying step together with the polymer gel, thereby raising impossibilities of the essential additive to be present in a sufficient amount in the drying step. Moreover, when the mixing is continued for a long period of time after completing the mixing, deterioration of performances of the resulting water absorbent resin may be caused such as increase in water extractables, lowering of the absorption capacity under a load, and the like of the water absorbent resin.

Exemplary means for accomplishing the mixing at a high speed may involve charging the heated aqueous fluid into the fine powder at once while stirring. In other words, when the aqueous fluid is gradually added by a method of, for example, spraying or the like, deterioration of the water absorbent resin may be caused because the fine powder may form a great aggregated block during the operation, or may be kneaded. Time period for charging the heated aqueous fluid is preferably not longer than 60 sec, more preferably not longer than 30 sec, and most preferably not longer than 10 sec. Also, as means for achieving the mixing at a high speed, a process in which the fine powder is charged into the heated aqueous fluid while stirring, contrary to the above process, may be also illustrated. In this instance, the time period for charging the fine powder is preferably not longer than 60 sec, more preferably not longer than 30 sec, and most preferably not longer than 10 sec. In addition, exemplary means for accomplishing the mixing at a high speed may also involve concurrently mixing the fine powder with the heated aqueous fluid at once. In this instance, time period for charging both of them is preferably not longer than 60 sec, more preferably not longer than 30 sec, and most preferably not longer than 10 sec. Also, the agglomerated particles can be also obtained continuously through concurrently charging both of them in continuity to allow for mixing at a high speed. The time period required for drying the agglomerated particles and the polymer gel while allowing them to coexist is preferably as short as possible, taking into account of the decomposition of the essential additive. When the polymer gel is obtained continuously in the polymerization step, the agglomerated particles are mixed therein continuously to subject to the drying step in a short time period in a preferred embodiment.

Whether the generated agglomerated matter is agglomerated particles or not may be ascertained by a optical microscopy based on the fact that a plurality of individual particles flock to aggregate while keeping their shape, and the fact that they are swollen as multiple discontinuous particles in absorption of a liquid.

Upon drying the agglomerated particles and the polymer gel while allowing them to coexist, the difference between the solid content rate (%) of the polymer gel and the solid content rate (%) of the agglomerated particles (or, difference between the moisture content rate of the polymer gel and the moisture content rate of the agglomerated particles) is preferably as small as possible. Specifically, ratio (A/B) of the solid content rate A (%) of the agglomerated particles (agglomerated gel) to the solid content rate B (%) of the polymer gel, in general, is preferably not less than 1/3 but not greater than 3, more preferably not less than 1/2 but not greater than 2, still more preferably not less than 2/3 but not greater than 3/2, yet more preferably not less than 4.5/5.5 but not greater than 5.5/4.5, and particularly preferably 1 (i.e., the solid contents being substantially the same). When the ratio (A/B) of the solid content rate A of the agglomerated particles to the solid content rate B of the polymer gel is out of the above range, drying of both components which had been mixed is liable to be heterogeneous. Thus, either one may be overdried or undried, thereby possibly causing troubles in production and problems in quality.

The term "solid content" refers to the residue yielded by eliminating volatile components (predominantly water) from the gelatinous water absorbent resin (polymer gel or agglomerated gel), i.e., resin component of the water absorbent resin. Herein, the weight of the solid content as described above is referred to as "quantity of solid content", while the ratio of the quantity of solid content per the weight of the gelatinous water absorbent resin including volatile components is represented by "solid content rate (%)". Also, the term "moisture content" refers to the proportion (%) of water included in the gelatinous water absorbent resin, corresponding approximately to the value derived by subtracting the aforementioned solid content (%) from 100%.

Upon drying while allowing the agglomerated particles and the polymer gel to coexist, ratio of the agglomerated particles to the polymer gel (in other words, recycling amount of the fine powder per the quantity of solid content in the polymer gel obtained in the polymerization step) is determined so that the quantity of solid content of the agglomerated particles (agglomerated gel), i.e., the quantity of solid content of the fine powder before the agglomeration, becomes preferably not greater than 40% by weight, and still more, to be not greater than 35% by weight, not greater than 30% by weight, not greater than 25% by weight, not greater than 20% by weight, not greater than 15% by weight is preferred in due order per the quantity of solid content in the polymer gel. Additionally, any lower limit is permissible as long as it is beyond 0% by weight. In general, it is considered that the recycling amount of the fine powder per the quantity of solid content in the polymer gel obtained in the polymerization step of beyond 40% by weight is not practical in light of the production efficiency.

Taking into consideration of the recycling amount of the fine powder being at most 40% by weight, the amount of the essential additive used through adding to the aqueous fluid is very small with respect to the entire water absorbent resin obtained after drying the agglomerated particles together with the polymer gel, which is at the very most lower than 0.3% by weight. When the recycling amount of the fine powder is approximately ten and several % by weight, the amount of the essential additive may be lower than 0.1% by weight. In other words, this method for production in which the essential additive is added to the aqueous fluid enables the residual monomer to be reduced to the desired level with a very small amount of the essential additive, in comparison with the cases in which lowering of the residual monomer to the desired level is intended through adding all the used essential additives to the polymer gel.

In this method for production, the agglomerated particles and the polymer gel are dried while allowing them to coexist. Preferably, it is desired to execute drying in the state in which at least a part of the agglomerated particles is brought into contact with at least a part of the polymer gel. Alternatively, it is preferred that the drying is executed through mixing the agglomerated particles with the polymer gel. The drying may be executed in the state of the agglomerated particles being homogenously mixed with the polymer gel, or in the state of the agglomerated particles being slightly mixed or hardly mixed with the polymer gel. In other words, according to this method for production, lowering of the residual monomer can be sufficiently accomplished by merely drying in the state of being slightly mixed or hardly mixed as described above, without particularly mixing to give a homogenous state. Specifically, in connection with the polymer gel that flows in a pipe or on a conveying belt connected to an apparatus for carrying out drying, for example, all needed is to allow the agglomerated particles to converge into the pipe or to supply on the conveying belt, followed by executing drying together as they stand. According to the prior arts in which a persulfate salt or the like is added to the polymer gel thereby reducing the residual monomer, it is important to homogeneously distribute the additive such as a persulfate salt or the like to the overall polymer gel. However, taking into account of separate operation of mixing also becoming necessary, it is indicated that the mechanisms of reducing the residual monomer may be distinct in this respect. In other words, according to this method for production, it is believed that the essential additive included in the agglomerated particles may not necessarily act on lowering of the residual monomer through being mixed homogenously with the polymer gel in the form of agglomerated particles, but it may exert some effect during drying. As a matter of course, it is anyhow permissible to homogeneously mix the agglomerated particles with the polymer gel.

In the agglomerated gel of the fine powder obtained in the aforementioned step (step disclosed in Japanese Patent Application No. 2005-38123), the particles thereof retain less amount of residual monomer. Therefore, upon pulverization for obtaining desired particle size distribution following the aforementioned drying step (drying step while allowing the aforementioned agglomerated gel and the aforementioned polymer gel to coexist), the fine powder (re-generated fine powder) derived from the agglomerated gel generated in the pulverizing step has lower amount of residual monomer compared to the fine powder (virgin fine powder) directly generated by drying and pulverization of the polymer gel. Consequently, total amount of residual monomer of fine particles having a particle size of, for example, smaller than 300 μm is reduced, therefore, difference in residual monomer, for example, between the particles having a particle size of 300 to 850 μm and particles having a particle size of smaller than 300 μm is decreased, thereby being capable of obtaining the water absorbing agent of the present invention having small RMI.

Content of the water absorbent resin regenerated in the aforementioned step included in the water absorbent resin particles of the present invention is preferably 0 to 50% by weight, more preferably 5 to 40% by weight, and most preferably 10 to 30% by weight. When the water absorbent resin regenerated in the above step was used as the water absorbent resin particle of the present invention, it may be advantageous in terms of performances because of greater surface area than unregenerated one thereby having a higher water absorption speed.

The aforementioned water absorbent resin precursor is adjusted to have a bulk density (specified by JIS K-3362, 1998) to fall within the range of 0.40 to 0.90 g/ml, more preferably 0.50 to 0.80 g/ml in order to obtain the water absorbing agent of the present invention. Also, it is adjusted to include the particles of 150 to 600 μm in an amount of preferably 90 to 100% by weight, more preferably 95 to 100% by weight, further preferably 98 to 100% by weight of total particles. Logarithmic standard deviation (a) of particle size distribution may be 0.20 to 0.50, more preferably 0.20 to 0.45, and particularly preferably 0.20 to 0.40.

The water absorbent resin precursor obtained in the present invention as described above may be adjusted to have the above-specified particle size distribution, and absorption capacity without load for a physiological saline solution before the surface crosslinking may be preferably not less than 32 g/g, more preferably 35 to 70 g/g, still more preferably 40 to 65 g/g, and particularly preferably 45 to 60 g/g. Regulation of the absorption capacity may be carried out through controlling the aforementioned polymerization conditions and drying conditions such as the internal crosslinking agent and the like.

To the water absorbent resin precursor obtained as described above is subjected to a surface crosslinking treatment for permitting crosslinking around the particle surface (third step). According to such a surface treatment, the water absorbing agent of the present invention can be obtained by lowering the absorption capacity without load (CRC: centrifuge retention capacity) to preferably 95 to 50%, and more preferably 90 to 60% of the absorption capacity without load (CRC) before the surface crosslinking.

As the surface crosslinking agent, a surface crosslinking agent which can form an ester bond with a carboxyl group is preferred. Illustrative examples of the surface crosslinking agent that forms an ester bond (preferably dehydrative ester bond) with a functional group (carboxyl group) of a polycarboxylic acid based water absorbent resin include surface crosslinking agents having a hydroxyl group in the molecule such as polyhydric alcohol or amino alcohol; and surface crosslinking agents that generate a hydroxyl group by opening the ring such as alkylenecarbonate, oxazolidinone, oxetane and epoxy compounds.

Examples of this surface crosslinking agent include polyhydric alcohol compounds such as ethylene glycol, diethylene glycol, triethylene glycol, tetraethylene glycol, polyethylene glycol, propylene glycol, 1,3-propanediol, 1-methyl-1, 3-propanediol, 2-methyl-1,3-propanediol, dipropylene glycol, 2,2,4-trimethyl-1,3-pentanediol, 2,3,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol, 1,2-cyclohexanemethanol, 1,2-cyclohexanedimethanol, 1,2-cyclohexanediol, trimethylolpropane, diethanolamine, triethanolamine, polyoxypropylene, oxyethylene-oxypropylene block copolymers, pentaerythritol, meso-erythritol, D-sorbitol and sorbitol; epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether and glycidol; polyamine compounds such as ethylenediamine, diethylenetriamine, triethylenetetramine, tetraethylenepentamine, pentaethylenehexamine, polyethyleneimine, polyamidepolyamine, and inorganic salts or organic salts (aziridinium salts and the like) thereof; polyisocyanate compounds such as 2,4-tolylene diisocyanate and hexamethylene diisocyanate; haloepoxy compounds such as epichlorohydrin, epibromohydrin and α-methyl epichlorohydrin; polyoxazoline compounds such as 1,2-ethylenebisoxazoline; oxazolidinone compounds such as N-acyl oxazolidinone and 2-oxazolidinone; alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1, 3-dioxane-2-one, 4,6-dimethyl-1,3-dioxane-2-one and 1,3-dioxopane-2-one; cyclic urea compounds; oxetane compounds such as oxetane, 2-methyloxetane, 3-methyl-3-hydroxymethyloxetane and 3-ethyl-3-hydroxymethyloxetane; polyvalent metal compounds such as hydroxides or chlorides of zinc, calcium, magnesium, aluminum, iron, zirconium or the like; and the like. Among these surface crosslinking agents, at least one compound selected from the group consisting of polyhydric alcohol compounds, epoxy compounds, polyamine compounds and salts thereof, oxetane compounds and alkylene carbonate compounds are suitable. More preferably, the surface crosslinking agent may be one or more compounds selected from the group consisting of polyhydric alcohols having 3 to 6 carbon atoms and including 2 to 3 hydroxyl groups in one molecule, epoxy compounds having 6 to 12 carbon atoms, alkylene carbonate having 3 to 5 carbon atoms, and oxetane compounds having 3 to 10 carbon atoms. One, or two or more of these surface crosslinking agents may be used taking into consideration of the reactivity. The surface crosslinking step may be carried out twice or more in light of the effect of the same. In this instance, the second and the following steps may be carried out using the same surface crosslinking agent as that in the first cycle, but they may be carried out using a different surface crosslinking agent.

As amino alcohol which can be used as the surface crosslinking agent, ethanolamine may be exemplified in addition to those described above.

Using amount of the surface crosslinking agent may be preferably not lower than 0.001 parts by weight but not higher than 10 parts by weight, and particularly preferably with the lower limit being 0.01 parts by weight and the upper limit being 5 parts by weight per 100 parts by weight of the water absorbent resin precursor powder, although it may vary depending on the used compound and the combination thereof. Use of the surface crosslinking agent within this range enables crosslinking density around the surface of the water absorbent resin to be higher than that inside thereof. The using amount of the surface crosslinking agent of beyond 10 parts by weight is not preferred because of not only economical inefficiency, but also excessive amount of necessary crosslinking agent upon forming an optimal cross-linked structure in an absorbing agent. The using amount of the surface crosslinking agent of lower than 0.001 parts by weight is not preferred because its improving effect of water-absorption properties such as the absorption capacity under a load and the like is hardly achieved in upgrading the same. When the surface crosslinking is executed, upon mixing of the water absorbent resin and the surface crosslinking agent, water is preferably used as a solvent. Using amount of water may be beyond 0 part by weight, preferably not higher than 20 parts by weight, and more preferably not lower than 0.5 parts by weight but not higher than 10 parts by weight per 100 parts by weight of the solid content of the water absorbent resin, although it may vary depending on the type, particle size, moisture content and the like of the water absorbent resin precursor.

When the surface crosslinking is executed, upon mixing of the water absorbent resin precursor and the surface crosslinking agent, a hydrophilic organic solvent may be used in combination as needed. Examples of the hydrophilic organic solvent which can be used in this step include lower alcohols such as methyl alcohol, ethyl alcohol, n-propyl alcohol, isopropyl alcohol, n-butyl alcohol, isobutyl alcohol and t-butyl alcohol; ketones such as acetone; ethers such as dioxane and tetrahydrofuran; amides such as N,N-dimethylformamide; and sulfoxides such as dimethylsulfoxide. Using amount of the hydrophilic organic solvent may vary depending on type, particle size, moisture content and the like of the water absorbent resin precursor, but may be preferably not lower than 0 part by weight but not higher than 20 parts by weight, and more preferably not lower than 0 part by weight but not higher than 10 parts by weight per 100 parts by weight of the water absorbent resin precursor powder. It is most preferred that the hydrophilic organic solvent is not used (substantially 0 part by weight) for the purpose of reducing source of impurities which may possibly cause a bad smell.

When the surface crosslinking is executed, a method in which after mixing water and/or the hydrophilic organic solvent with the surface crosslinking agent beforehand, the aqueous solution is mixed by spraying or adding dropwise to the water absorbent resin precursor is preferably employed. A method in which mixing by spraying is conducted is more preferred. Size of the sprayed droplet may fall within preferably the range of 0.1 to 300 µm, and more preferably the range of 0.1 to 200 µm in terms of mean particle size.

Mixing apparatus used in mixing the water absorbent resin precursor and the surface crosslinking agent, and water and hydrophilic organic solvent preferably has great mixing force for homogenously and reliably mixing them. Suitable examples of the mixing apparatus include, e.g., cylindrical mixers, conical double wall mixers, high speed stirring mixers, V-shaped mixers, ribbon mixers, screw mixers, double arm kneaders, pulverizing kneaders, rotary mixers, airflow mixers, turbulizers, batch type ledge mixers, continuous ledge mixers and the like.

When the surface crosslinking is executed, after mixing the water absorbent resin precursor and the surface crosslinking agent, a heat treatment is further carried out to permit the crosslinking around the surface of the water absorbent resin precursor, thereby obtaining the water absorbent resin. More specifically, for allowing the crosslinking agent to be reacted around the surface of the water absorbent resin precursor, it is preferred to carry out the heat treatment in light of the reactivity of the crosslinking agent, simplicity of the apparatus for production and productivity. Treatment temperature of the heat treatment is preferably not lower than 80° C. but not higher than 250° C. as the temperature of the material although it may vary depending on the employed crosslinking agent. The treatment temperature of lower than 80° C. is not preferred because time period required for the heat treatment may be so long that lowering of productivity may be caused, and in addition, homogenous surface crosslinking cannot be achieved, thereby being liable to cause deterioration of absorption properties under a load, and remaining of the surface crosslinking agent. Also, the treatment temperature of higher than 250° C. is not preferred because the water absorbent resin precursor may cause heat deterioration per se.

Apparatus used for carrying out the heat treatment may be known dryer or heating oven. Suitable examples include e.g., conductive heat transfer type, radiation heat transfer type, hot air heat transfer type, dielectric heat type dryers or heating ovens. Specifically, belt type, grooved stirring type, screw type, rotary type, disk type, kneading type, fluidized bed type, airflow type, infrared radiation type, electron beam type dryer or heating oven may be exemplified.

Although fine powder may be generated again due to damage caused in the process following the heat treatment, it may be removed by further providing a classification step well before obtaining the final product and may be preferably subjected to particle size enlarging step (agglomeration step; aforementioned step of regeneration to give larger particles or agglomerates in particulate form) together with the fine powder which had been obtained in the classification step of the pulverized particles before the heating treatment. In connection with the fine powder subjected to the particle size enlarging step, proportion of the amount of the fine powder after the heat treatment to the amount of the fine powder before the heat treatment may be preferably not greater than 5% by weight, and more preferably not greater than 3% by weight. The proportion of the amount of the fine powder after the heat treatment beyond 5% by weight is not preferred because strength of the particle size-enlarged particles is liable to be lowered, and the absorption capacity may be also declined.

To the water absorbent resin obtained as described above, if necessary, is added by spraying an aqueous solution that includes a sulfur-containing reducing agent (fourth step). Particularly, this method can be employed in the step of recovering fine particles containing a large amount of residual monomer described above for obtaining the water absorbing agent having low amount of residual monomer and having small variance of the amount of residual monomer among the ranges of particle size distribution, without using the technique for recovering through reducing the residual monomer of the fine particles (Japanese Patent Application No. 2005-38123).

The surface crosslinking is characterized by enabling selective and preferential addition of a small amount of an aqueous solution to the particle surface and fine particles. In the aqueous solution can be included a chelating agent, a plant component, an antimicrobial agent, a water soluble polymer, an inorganic salt or the like described later. Amount of water in which the sulfur-containing reducing agent is to be dissolved may be not lower than 0.5 parts by weight but not higher than 15 parts by weight, more preferably not lower than 1 part by weight but not higher than 12 parts by weight, still more preferably not lower than 1 part by weight but not higher than 10 parts by weight, and particularly preferably not lower than 1 part by weight but not higher than 5 parts by weight per 100 parts by weight of the water absorbent resin. When the amount of water is lower than the aforementioned lower limit, 0.5 parts by weight, homogenous mixing of the aqueous solution that includes a sulfur-containing reducing agent with the water absorbent resin may be difficult. Moreover, the amount beyond the upper limit, 15 parts by weight, is not preferred because excessive energy for drying is required in adjusting to give a desired moisture content as described later, thereby leading to diseconomy. Also, it is not preferred in light of stable production because handling of the mixture following mixing of the aqueous solution may be difficult. Furthermore, when the amount is beyond the upper limit, 15 parts by weight, unpleasant odor may be developed during drying at a high temperature for adjusting to give a desired moisture content in a short period of time. Additionally, when water in an amount of not lower than the upper limit, 15 parts by weight is added, the water absorbent resin may aggregate rigidly, thereby necessitating pulverization after drying. According to this repulverizing step, surface crosslinked layer which had been already formed may be destroyed, and thus, desired absorption capacity under a load may not be possibly achieved.

Moreover, amount of the sulfur-containing reducing agent may be preferably not lower than 0.05 parts by weight but not higher than 10 parts by weight, and more preferably not lower than 0.1 parts by weight but not higher than 8 parts by weight per 100 parts by weight of the water absorbent resin. When the using amount of the sulfur-containing reducing agent is lower than the aforementioned lower limit, 0.05 parts by weight, desired effect to reduce the residual monomer may not be achieved. In contrast, the using amount beyond the upper limit, 10 parts by weight, will be excessive amount of addition for required effect to reduce the residual monomer, and may be possibly accompanied by deterioration of physical properties and may be uneconomical in terms of costs. Also, it is preferred that the additive that includes the sulfur-containing reducing agent accounts for not lower than 0.001% by weight but not higher than 50% by weight in the aqueous solution. In the present invention, a small amount is sufficient because selective and preferential addition onto/into the particle surface and the fine particles is perfected without deteriorating physical properties.

Examples of the sulfur-containing reducing agent include sodium sulfite, potassium sulfite, calcium sulfite, ammonium sulfite, sulfurous acid, sodium hydrogen sulfite, potassium hydrogen sulfite, ammonium hydrogen sulfite, sodium thiosulfate, potassium thiosulfate, ammonium thiosulfate, magnesium thiosulfate, cysteine, cystine and the like. One or two or more among these may be used. Among these, sulfite salts and hydrogen sulfite salts are preferred in light of the effect to reduce the residual monomer and cost.

The aqueous solution that includes the sulfur-containing reducing agent can be obtained by supplying in a droplet state to the water absorbent resin and mixed therein. It is more preferred to be mixed while being controlled to give minute droplet diameter by spraying. Mean particle size of the sprayed droplet is preferably not smaller than 0.1 µm but not larger than 300 µm, and more preferably, the upper limit is 200 µm. Although any problem is not particularly caused even though the droplet has a mean particle size of smaller than 0.1 µm, it will not be common because selectable spray nozzle is limited, and selection of the apparatus could necessitate very expensive design of the apparatus. Furthermore, when the droplet has a mean particle size of beyond 300 µm, number of droplets per unit volume of the aqueous solution may be decreased. Accordingly, probability of encounter with the water absorbent resin to be mixed may be decreased to result in failure in achieving homogeneous mixing. Therefore, even though the effect to reduce the amount of residual monomer is achieved, variance of the amount of residual monomer among the particles is generate, and failure in yielding desired residual monomer index may be resulted.

The mixing apparatus used for addition of the aqueous solution preferably has great mixing force. Examples of this mixing apparatus include e.g., cylindrical mixers, conical double wall mixers, high speed stirring mixers, V-shaped mixers, ribbon mixers, screw mixers, double arm kneaders, pulverizing kneaders, rotary mixers, airflow mixers, turbulizers, batch type ledige mixers, continuous ledige mixers and the like.

In adding the aqueous solution by spraying, the aqueous solution that includes a sulfur-containing reducing agent may further include other additive such as a chelating agent, a plant component, an antimicrobial agent, a water soluble polymer, an inorganic salt or the like described later. Content of the additive in this instance may be freely selected as needed, but may account for not lower than 0.001% by weight but not higher than 50% by weight of the aqueous solution. As the chelating agent, a chelating agent having high sequestering ability and chelating ability against Fe and Cu is preferred. Specific examples include chelating agents having stability constant against Fe ion of not less than 10, preferably a chelating agent having a stability constant of not less than 20, more preferably aminopolyvalant carboxylic acids and salts thereof, and particularly preferably aminocarboxylic acids and salts thereof having 3 or more carboxyl groups. Specific examples of these polyvalent carboxylic acids include diethylenetriamine pentaacetic acid, triethylenetetraamine hexaacetic acid, cyclohexane-1,2-diamine tetraacetic acid, N-hydroxyethylethylenediamine triacetic acid, ethyleneglycol diethyl ether diamine tetraacetic acid, ethylenediamine tetrapropionacetic acid, N-alkyl-N'-carboxymethyl aspartic acid, N-alkenyl-N'-carboxymethyl aspartic acid and alkali metal salts, alkaline earth metal salts; ammonium salts or amine salts thereof. The salt may be either completely neutralized or partially neutralized, or a mixture thereof is also permitted. Among them, diethylenetriamine pentaacetic acid, triethylenetetraamine hexaacetic acid, N-hydroxyethylethylenediamine triacetic acid and a salt thereof are most preferred. In addition, using amount of the same may be usually 0.00001 to 10 parts by weight, and preferably 0.0001 to 1 part by weight per 100 parts by weight of the water absorbent resin.

The aforementioned plant component may be blended in the range of 0 to 10 parts by weight, preferably 0.001 to 5 parts by weight, and more preferably 0.002 to 3 parts by weight per 100 parts by weight of the water absorbent resin, for the purpose of exerting the deodorizing performance. The plant component which can be used in the present invention may be preferably at least one compound selected from polyphenol, flavone and their analogues and caffeine, and more preferably at least one component selected from tannin, tannic acid, Chinese gallbut, gallnut and gallic acid. Moreover, the aforementioned antimicrobial agent is not particularly limited, but may be any known antimicrobial agent having an antibacterial activity, and examples thereof include antimicrobial agents disclosed in, for example, JP-A No. H11-267500.

The water absorbent resin to which the aqueous solution that includes a sulfur-containing reducing agent was added is subjected to a treatment of drying by heating, thereby obtaining a water absorbing agent in the state of agglomerate (fifth step). In light of the agglomeration strength, the heat treatment may be carried out such that moisture content, which is specified by dividing the weight loss after drying yielded through heating at 180° C. for 3 hrs by the weight before the drying, of not lower than 1% by weight but not higher than 15% by weight. Lower limit of the moisture content may be preferably 2% by weight, and particularly preferably 2.5% by weight, while the upper limit may be preferably 13% by weight, and particularly preferably 12% by weight.

For the heating, a heat medium of airflow such as hot air may be used. The heat temperature (heat medium temperature or material temperature) may be preferably not lower than 40° C. but not higher than 120° C., and more preferably, the lower limit being 50° C. and the upper limit being 100° C. The heating time may be preferably not shorter than 1 min but not longer than 2 hrs. Suitable examples of combination of the heat temperature and the heating time include: at 60° C. for 0.1 to 1.5 hours, at 100° C. for 0.1 to 1 hour, and the like. When the condition is out of this range, the case of too low temperature and too short time period not falling within this range is not preferred because state of the surface of the resulting water absorbing agent may be so wet that strong adhesiveness is provided, thereby involving difficulty in handling as powder. In contrast, the case of too high temperature and too long time period not falling within this range is not preferred because of diseconomy in terms of energy, as well as possible lowering of absorption capacity through the crosslinking reaction proceeded resulting from the surface crosslinking agent slightly remained on/in the water absorbing agent.

Addition of the aqueous solution and heating may be carried out either in the same apparatus, or in different apparatuses. The heating may be carried out either wile stirring or while standing still (substantially without stirring), as long as the temperature and moisture content can be regulated to fall within the predetermined range, however, it is preferably carried out while standing still to permit curing to allow formation of loose block. The heating may be carried out after overlaying the water absorbent resin to which the aqueous solution was added to have a thickness of approximately 1 to 100 cm. Lower limit of the thickness may be preferably 5 cm, and particularly preferably 10 cm, while the upper limit may be preferably 80 cm, and particularly preferably 70 cm. Thus cured water absorbing agent may be further subjected to pulverization, or classification as needed to give the water absorbing agent according to the present invention. The curing described above is defined as operation for excluding wettability of the surface of the water absorbing agent particles to give powder in the aforementioned heat treatment step.

In the present invention, (A) a plant component, (B) a polyvalent metal salt of an organic acid, (C) inorganic fine particles (including (D) composite hydrated oxide) or the like may be further added as a minor constituent, in addition to the chelating agent, plant component and antimicrobial agent described hereinabove. Accordingly, various functions can be also imparted to the water absorbing agent of the present invention.

Using amount of these (A) to (D) and (E) other additives may vary depending on object and function to be imparted, however, the amount may fall within the range of generally 0 to 10 parts by weight, preferably 0.001 to 5 parts by weight, and still more preferably 0.002 to 3 parts by weight based on the addition amount of one compound, per 100 parts by weight of the water absorbent resin. In general, the amount of lower than 0.001 parts by weight may not result in sufficient effect and function to be additionally imparted, while the amount of not lower than 10 parts by weight may not result in appropriate effect in view of the addition amount, or may lead to deterioration of the absorption performance.

(A) Plant Component

In the water absorbing agent according to the present invention can be blended a plant component in the aforementioned amount in order to allow deodorizing performance to be exerted. Examples of the plant containing a plant component other than the aforementioned plant components include e.g., *Camellia japonica* (camellia), *Eurya japonica* and *Ternstroemia japonica* and the like in theaceous plants, *Oryza sativa* (rice), bamboo grass, bamboo plant, *Zea mays* (corn), wheat and the like in poaceous plants, and coffee plant in rubiaceous plants, and the like. Form of the plant component used in the present invention may be extract obtained from the plant (essential oil), the plant itself, plant residue and extraction residue of the plant yielded as by products in production steps in plant-processing industry and food-processing industry, and the like, but not particularly limited thereto.

(B) Polyvalent Metal Salt

In the water absorbing agent according to the present invention can be blended a polyvalent metal salt, particularly a polyvalent metal salt of an organic acid in the aforementioned amount for improving powder flow performances, and for preventing blocking in moisture absorption. The polyvalent metal salt of an organic acid which may be used and mixing method are illustratively shown in, for example, International Application No. PCT/2004/JP1355, disclosing metal salts, other than alkali metal salts, of a fatty acid, a petroleum acid, a high molecular acid or the like, as a polyvalent metal salt of an organic acid having 7 or more carbon atoms in the molecule, which may be used in the present invention. Illustrative examples of the organic acid constituting the polyvalent metal salt of the organic acid include long chain or branched fatty acids such as caproic acid, octylic acid, octynoic acid, decanoic acid, lauric acid, myristic acid, palmitic acid, oleic acid and stearic acid; petroleum acids such as benzoic acid, myristic acid, naphthene acid, naphthoic acid and naphthoxyacetic acid; high molecular acids such as poly (meth)acrylic acid, and polysulfonic acid. However, organic acids having a carboxyl group within the molecule are preferred, and fatty acids such as caproic acid, octylic acid, octynoic acid, decanoic acid, lauric acid, myristic acid, palmitic acid, oleic acid, stearic acid, beef fatty acid and hydrogenated castor oil are more preferred. The organic acid may be more preferably a fatty acid not having an unsaturated bond in the molecule, for example, caproic acid, octylic acid, decanoic acid, lauric acid, myristic acid, palmitic acid and stearic acid. Most preferably, the organic acid may be a long chain fatty acid having 12 or more carbon atoms in the molecule and not having an unsaturated bond, for example, lauric acid, myristic acid, palmitic acid or stearic acid.

(C) Inorganic Fine Particle

In the water absorbing agent according to the present invention can be blended inorganic fine particles, particularly water insoluble inorganic fine particles for preventing blocking in moisture absorption. Specific examples of the inorganic particles which may be used in the present invention include e.g., metal oxides such as silicon dioxide and titanium oxide, silicic acid (silicate) such as natural zeolite and synthetic zeolite, kaolin, talc, clay, bentonite and the like. Among them, silicon dioxide and silicic acid (silicate) are more preferred, and silicon dioxide and silicic acid (silicate) having a mean particle size of 0.001 to 200 µm as measured by Coulter counter method are still more preferred.

(D) Composite Hydrated Oxide

In the water absorbing agent according to the present invention can be blended a composite hydrated oxide including zinc and silicon or zinc and aluminum for allowing excellent flowability after moisture absorption (flowability of powder after the water absorbent resin or the water absorbing agent absorbed moisture) to exhibit, and further allowing excellent deodorizing function to be exerted.

For example, the water absorbing agent according to the present invention obtained by the aforementioned method for production as one example has the amount of residual monomer determined by quantitative determination with HPLC (high performance liquid chromatography) described later being not lower than 0 but not higher than 500 ppm. The amount of residual monomer is preferably not lower than 0 but not higher than 400 ppm, more preferably not lower than 0 but not higher than 300 ppm, more preferably not lower than 0 but not higher than 250 ppm, more preferably not lower than 0 but not higher than 200 ppm, still preferably not lower than 0 but not higher than 150 ppm, and particularly preferably not lower than 0 but not higher than 100 ppm. When the main component of the monomer used in the polymerization described above is acrylic acid and/or a salt thereof, content of unreacted acrylic acid and/or a salt thereof is not higher than 500 ppm. When the amount of residual monomer of the water absorbing agent of the present invention is beyond 500 ppm, bad smell may be emitted after absorbing human urea in practical use as an absorbing article such as a diaper followed by swelling. Furthermore, taking into account of possibility of contact with the user's skin, problems in sanitary aspects may be also involved. Additionally, this amount is not preferred also because bad influence may be exerted on health of the worker due to scattered powder in manufacturing site of the absorbing article.

For example, the water absorbing agent according to the present invention obtained by the aforementioned method for production as one example has a residual monomer index (RMI) determined by the following formula (1) being not greater than 0.30. RMI is preferably, not less than 0 but not greater than 0.26, more preferably, not less than 0 but not greater than 0.20, still more preferably not less than 0 but not greater than 0.15, and particularly preferably, not less than 0 but not greater than 0.10.

$$RMI = |RM_1 - RM_2|/RM_A \quad (1)$$

wherein, $RM_1$ represents the amount of residual monomer of the water absorbing agent having a particle size of smaller than 300 μm among the particles constituting the water absorbing agent; $RM_2$ represents the amount of residual monomer of the water absorbing agent having a particle size of 300 to 850 μm among the particles constituting the water absorbing agent; and $RM_A$ represents the amount of residual monomer of the water absorbing agent. When $RM_A$ is 0, RMI shall be 0.

The residual monomer index herein may be determined by: subjecting the water absorbing agent to sieve classification using JIS standard sieves having mesh opening size of 850 μm and 300 μm, and a tray; determining the amount of residual monomer of particles having a particle size of smaller than 300 μm, and of particles having a particle size of 300 to 850 μm, respectively; and substituting for them together with the value of the residual monomer of the water absorbing agent as determined described above in the formula (1). This residual monomer index beyond 0.30 is not preferred because it is suggested that there exists the variance of the amount of residual monomer among ranges of particle size distribution of the water absorbing agent, and thus, variance of the amount of residual monomer is caused on the basis of the difference in particle size distribution of the water absorbing agent resulting from particle segregation, when this water absorbing agent is used in an absorbing article.

It is preferred that the water absorbing agent of the present invention has an absorption capacity without load (CRC) for a physiological saline solution as measured with the method described later is not less than 30 g/g. When the absorption capacity without load is less than 30 g/g, high absorption property may not be exhibited when it is used in an absorbing article such as a diaper. In contrast, the upper limit is not limited, but approximately 60 g/g is believed to be enough in light of difficulty in production and costs. CRC may be more preferably not less than 31 g/g but not greater than 55 g/g, and particularly preferably not less than 32 g/g but not greater than 50 g/g. When regulation of the absorption capacity without load (CRC) of the water absorbing agent of the present invention is intended to be not less than 30 g/g, regulation should be conducted to attain not less than 30 g/g in anticipation of lowering of water absorbing capacity of the water absorbent resin before addition of the aqueous solution that includes a sulfur-containing reducing agent in the fourth step, i.e., the water absorbent resin crosslinked on the surface thus obtained in the third step, in an amount corresponding to the added aqueous solution.

It is preferred that the water absorbent resin of the present invention has an absorption capacity under a high load of 4.8 kPa (AAP 4.8 kPa) for a physiological saline solution as measured with the method described later is not less than 20 g/g. When this absorption capacity under a high load is less than 20 g/g, high absorption property may not be exhibited when it is used in an absorbing article such as a diaper. In contrast, the upper limit is not limited, but approximately 35 g/g is believed to be enough in light of difficulty in production and costs. The absorption capacity under a high load may be more preferably not less than 21 g/g, and particularly preferably not less than 22 g/g.

When regulation of the absorption capacity under a high load (AAP 4.8 kPa) of the water absorbing agent of the present invention is intended to be not less than 20 g/g, regulation should be conducted to attain not less than 20 g/g in anticipation of lowering of water absorbing capacity of the water absorbent resin before addition of the aqueous solution that includes a sulfur-containing reducing agent in the fourth step, i.e., the water absorbent resin crosslinked on the surface thereof obtained in the third step, in an amount corresponding to the added aqueous solution.

The water absorbing agent of the present invention regulated to have the absorption capacity without load of not less than 30 g/g and the absorption capacity under a high load of not less than 20 g/g often has comparatively superior gel strength. Therefore, in the case of use in an absorbing article, particularly in an absorbing article constituted with the water absorbing agent and a hydrophilic fiber as the main component, it is suitably used in the absorbing article having a high content of the water absorbing agent (core concentration) per total weight of the water absorbing agent and the hydrophilic fiber. In this instance, the core concentration may be preferably 30 to 100% by weight, more preferably 40 to 90% by weight, and most preferably 50 to 80% by weight.

In the water absorbing agent of the present invention, when regulation of the absorption capacity without load to be not less than 30 g/g and the absorption capacity under a high load to be not less than 20 g/g is specified as an arbitrary option, as an alternative parameter, total absorption capacity (TAC) for a physiological saline solution which is calculated by substituting for the absorption capacity without load (CRC) and a single-layer absorption capacity under a load of 1.9 kPa (SAAP) as measured by the method described later in the following formula (2) is preferably not less than 65 g/g. The total absorption capacity may be more preferably not less than 67 g/g, and particularly preferably not less than 70 g/g. This total absorption capacity of less than 65 g/g is not preferred because high absorption property may not be exhibited when it is used in an absorbing article such as a diaper. Although the upper limit is not limited, approximately 100 g/g is believed to be enough in light of difficulty in production and costs.

$$TAC\ (g/g) = CRC + SAAP \quad (2)$$

wherein, CRC represents absorption capacity without load (g/g), and SAAP (Single-layer AAP) represents single-layer absorption capacity under a load of 1.9 kPa (g/g).

When regulation of the total absorption capacity (TAC) of the water absorbing agent of the present invention is intended to be not less than 65 g/g, regulation should be conducted to attain not less than 65 g/g in anticipation of lowering of water absorbing capacity of the water absorbent resin before addition of the aqueous solution that includes a sulfur-containing reducing agent in the fourth step, i.e., the water absorbent resin crosslinked on the surface thereof obtained in the third step, in an amount corresponding to the added aqueous solution.

The water absorbing agent of the present invention having the total absorption capacity for a physiological saline solution of not less than 65 g/g often has higher absorption capacity without load in comparison with the aforementioned water absorbing agent regulated to have the absorption capacity without load of not less than 30 g/g and the absorption capacity under a high load of not less than 20 g/g. Therefore, use in a comparably low core concentration than the aforementioned core concentration used in the absorbing article is preferred because desired absorption capacity of the absorbing article can be achieved with less amount of the water absorbing agent. In this instance, the core concentration may be preferably 10 to 70% by weight, more preferably 20 to 60% by weight, and most preferably 30 to 50% by weight.

When the water absorbing agent regulated to have the absorption capacity without load of not less than 30 g/g and the absorption capacity under a high load of not less than 20 g/g, and the water absorbing agent regulated to have the total absorption capacity of not less than 65 g/g may be water absorbing agents that meet their parameter either separately or concurrently.

The present inventor found that the amount of residual monomer of the water absorbing agent varies among the ranges of particle size distribution, which had not been known conventionally, and according to comparison of the amount of residual monomer on each range of particle size distribution, it was found that the amount of residual monomer varies greatly on the particle size of 300 μm, and that the amount of residual monomer further varies greatly on the particle size of approximately 150 μm. Therefore, for regulating the residual monomer index of the present invention to fall within a particular range, it is important to strictly control particle size distribution, i.e., weight ratio of particles having a particle size of 300 to 850 μm to particles having a particle size of smaller than 300 μm, and the amount of fine particles having a particle size of smaller than 150 μm. When such values are out of the specific range described below, regulation of the residual monomer index may be difficult.

Moreover, when the water absorbing agent included in thin disposable absorbing articles such as diapers, which have been preferred in recent years, has too large particle size, for example, when a large number of particles having a particle size of beyond 850 μm are included, the coarse particles of the water absorbing agent may irritate the wearer's skin, and increase unpleasantness experienced by the wearer. Therefore, the water absorbing agent including too large number of coarse particles having a large particle size is not preferred for absorbing articles.

Furthermore, the particle size distribution and the mass median particle size of a water absorbing agent closely correlate with the value of surface area of the water absorbing agent. The surface area of the water absorbing agent corresponds to contact area between the water absorbing agent and the aqueous liquid such as body fluid, and exerts great influences on water absorbing behavior and the absorption ability as described above of the water absorbing agent. When the number of the fine particles are too large, gel blocking can be caused to possibly reduce the absorption ability of the absorbing article. In addition, possibility of deterioration of working environment may be increased due to scattering of dust in production of the absorbing article. In contrast, when the number of coarse particles is too large, absorption ability of the absorbing article may be reduced due to lowered water absorption speed caused by decrease of the surface area of the water absorbing agent.

Accordingly, control of the particle size distribution of the water absorbing agent is also important in light of regulation of the absorption ability of the water absorbing agent, and also in light of finish of the absorbing article and working environment. Therefore, in consideration of the aforementioned circumstances, the water absorbing agent of the present invention is strictly controlled to fall within the following scope.

The water absorbing agent of the present invention is controlled to include not less than 95% by weight of the particles having a particle size of not larger than 850 μm in the entire water absorbing agent, and to have the content of the particles of smaller than 150 μm being not higher than 5% by weight, preferably not higher than 2% by weight, and more preferably not higher than 1% by weight. Weight ratio of the particles having a particle size of 300 to 850 μm to the particles having a particle size of smaller than 300 μm may be not less than 5/95 but not greater than 95/5, more preferably not less than 20/80 but not greater than 80/20, and still more preferably not less than 30/70 but not greater than 70/30. Moreover, it is preferred to be controlled such that the particles having a particle size of not smaller than 150 μm but not larger than 600 μm account for not less than 90% by weight, further not less than 95% by weight, and particularly not less than 98% by weight of the entire water absorbing agent.

The water absorbing agent is controlled to have a mass median particle size (D50) in a narrow range of preferably 200 to 710 μm, more preferably 250 to 600 μm, and particularly preferably 300 to 500 μm, and controlled to have proportion of the particles of smaller than 150 μm being 0 to 5% by weight, preferably 0 to 3% by weight, and more preferably 0 to 2% by weight, and particularly preferably 0 to 1% by weight. In addition, mass median particle size of the water absorbing agent after agglomeration in the fourth step and fifth step may be increased by 5 to 30% over the mass median particle size of the water absorbent resin before the agglomeration. It is preferred that lower limit of percent of rise in this instance may be 7%, and particularly 9%, while the upper limit may thereof be 25%, and particularly 20%. Because the method for production of the present invention has an agglomeration step, the water absorbing agent is characterized by having a small content of fine particles, for example, those having a particle size of smaller than 150 μm despite of the mass median particle size being so small.

Logarithmic standard deviation ($\sigma\zeta$) of this particle size distribution of the water absorbing agent is controlled to be not less than 0.20 but not greater than 0.50. It is more preferred that the upper limit may be preferably 0.45, and particularly 0.40.

Bulk density (specified by JIS K-3362, 1998) of the water absorbing agent of the present invention may be controlled to be not less than 0.40 g/ml but not greater than 0.90 g/ml. It is more preferred that the lower limit of the bulk density is controlled to be 0.50 g/ml, while the upper limit is controlled to be 0.80 g/ml.

This water absorbing agent preferably has an irregular pulverized shape for fixing ability to a hydrophilic fiber such as pulp. The irregular pulverized shape refers to that of pulverized matter, preferably the pulverized matter in aqueous polymerization and having the aforementioned particle size distribution.

Moreover, this water absorbing agent has content of the sulfur based volatile component specified by the method for measurement described later being preferably 0 to 2.5 ppm, more preferably 0 to 2.0 ppm, further preferably 0 to 1.5 ppm, still more preferably to 1.0 ppm, and particularly preferably 0 ppm (undetectable). When the sulfur based volatile component is detected to be beyond the aforementioned upper limit of 2.5 ppm, it is concluded that odor derived from the sulfur-containing reducing agent added in the foregoing step is emitted from the swollen gel. In this case, when it is put into practical use for absorbing articles, the wearer may experience unpleasantness, and also involves disadvantage in sanitary aspects.

When the aqueous solution that includes a sulfur-containing reducing agent is added to the water absorbent resin after the surface crosslinking treatment to obtain a water absorbing agent for the purpose of reducing the amount of residual monomer, absorption properties of the resulting water absorbing agent must be sufficiently considered, in addition to regulation of the amount of sulfur based volatile component in the resulting water absorbing agent to fall within the above range. In this respect, detailed description will be made below.

For regulating the amount of sulfur based volatile component in the resulting water absorbing agent to fall within the above range, the aqueous solution and the water absorbent resin after the surface crosslinking treatment must be mixed as homogeneously as possible, and the means used therefor may be preferably a mixing apparatus having a great mixing force as described above. However, in the mixing apparatus having a great mixing force, previously formed surface crosslinked layer may be destroyed due to process damage brought to the water absorbent resin from the apparatus. In particular, when the aqueous solution that includes a sulfur-containing reducing agent is supplied in a comparatively large droplet state to the water absorbent resin, and probability of encounter with the water absorbent resin is low, the water absorbent resin failed to come in contact with the droplet is subjected to "null mixing", generally referred to, in the mixing apparatus. Hence, the surface crosslinked layer which turned into a dried state after the heat treatment step is scraped away by the wall face and the stirring member of the mixing apparatus. As a consequence, the resulting water absorbing agent exhibits remarkably decreased absorption capacity under a high load (AAP 4.8 kPa) physical characteristic value of which being greatly affected by homogeneity of the surface crosslinkage. Thus, it was hitherto difficult to obtain a water absorbing agent having an absorption capacity under a high load (AAP 4.8 kPa) kept at a particular level while having a particular absorption capacity without load (CRC). More specifically, among the water absorbing agents including the surface-crosslinked water absorbent resin and the sulfur-containing reducing agent, any water absorbing agent having a particular absorption capacity without load (CRC) and a particular absorption capacity under a high load (AAP 4.8 kPa), while concurrently exhibiting the amount of sulfur based volatile component regulated to fall with in the specified range could not have conventionally existed.

However, upon addition of the aqueous solution that includes a sulfur-containing reducing agent to the water absorbent resin after the surface crosslinking, when the aqueous solution is mixed by spraying with the droplet diameter falling within the aforementioned preferred range as in accordance with the method for production of the present invention, to obtain a water absorbing agent that could not have been obtained hitherto was enabled. More specifically, it became possible to obtain a water absorbing agent having an absorption capacity without load (CRC) of not less than 32 g/g, and an absorption capacity under a high load (AAP 4.8 kPa) of not less than 20 g/g, while concurrently exhibiting the amount of sulfur based volatile component regulated to fall within especially strict region of 0 to 3 ppm. Furthermore, addition of the aqueous solution enables obtaining the water absorbing agent with the amount of residual monomer reduced to fall within a desired range. Details of the grounds for absorption properties of the water absorbing agent obtained by the method for production of the present invention being able to be kept at high level are uncertain. However, it is presumed that gel elasticity was elevated through slightly turning the surface of the water absorbent resin into the wet/swollen state and that the surface crosslinked layer became resistant to destruction by the process damage brought thereto from the wall face and the stirring member of the mixing apparatus, as a result of increased probability of encounter between the water absorbent resin and the droplet of the aqueous solution by virtue of the method as described above.

Moreover, the water absorbing agent of the present invention has a brightness by Hunter of not less than 70, preferably not less than 71, and more preferably not less than 72. The moisture content may be 1 to 15% by weight per the total weight.

Although applications of the water absorbing agent of the present invention are not particularly limited, but preferably, it can be used in absorbing articles such as disposable diapers, sanitary napkins and incontinence pads. In particular, excellent performances may be achieved when it is used in diapers having high concentration of water absorbing agent (those in which a large quantity of a water absorbent resin is used in a piece of diaper) which have conventionally involved problems of the odor, coloring and the like derived from the raw material of the water absorbing agent.

The absorbing article of the present invention has an absorbent core obtained by forming the water absorbing agent, and a hydrophilic fiber as needed to give a sheet shape; a front face sheet having liquid permeability; and a back face sheet having liquid impermeability. When the hydrophilic fiber is not used, the absorbent core may be constituted by fixing the water absorbing agent on paper and/or nonwoven fabric. The absorbing articles of the present invention, in particular, disposable diapers for children, disposable diapers for adults and sanitary napkins can be fabricated by, for example, producing the absorbent core (absorbing core) through blending or sandwiching fiber substrate and the water absorbing agent of the present invention, followed by sandwiching the absorbing core between a substrate with liquid permeability (the front face sheet) and a substrate with liquid impermeability (the back sheet) and mounting of elastic parts, diffusion layers, pressure sensitive adhesive tapes, and the like, if necessary.

Content of the water absorbing agent (core concentration) in the absorbent core in this absorbing article may be preferably not lower than 10% by weight, more preferably not lower than 20% by weight, still more preferably not lower than 30% by weight, and particularly preferably not lower than 70% by weight. Also, aforementioned absorbent core is preferably subjected to compression molding to have the density of not less than 0.06 g/cc but not greater than 0.50 g/cc, and basis weight of not less than 0.01 g/cm$^2$ but not greater than 0.20 g/cm$^2$. Examples of the fiber base material which can be used include e.g., ground wood pulp, cotton linters, and hydrophilic fibers such as cross-linked cellulosic fibers, rayon fibers, cotton fibers, wool fibers, acetate fibers, vinylon fibers, and the like, which are preferably airlied.

Because the absorbing article of the present invention includes a water absorbing agent having a low amount of residual monomer and small variance of the amount of residual monomer among ranges of particle size distribution, the amount of residual monomer in the entire article is low, thus achieving small variance of the amount of residual monomer among articles. Because the amount of residual monomer is low, sanitary absorbing articles can be formed even though they are of slim type.

EXAMPLES

Hereinbelow, advantages of the present invention will be demonstrated by way of Examples, however, the present invention should not be construed as being limited by description of these Examples. Various performances of the water absorbing agent were measured by the following method. Also in the cases in which various performances of commercially available water absorbent resins and water absorbing agent, as well as water absorbing agents removed from diapers and the like are measured, similar method for measurement may be employed. In addition, upon comparative tests of commercially available water absorbent resins and water absorbing agents as well as water absorbing agents removed from diapers and the like carried out by way of comparison, when they had absorbed moisture in distribution process, they may be subjected to drying under reduced pressure ad libitum (for example, at 60 to 80° C. for approximately 16 hours) thereby drying the water absorbing agent to give an equilibrium moisture content (approximately 5% by weight, 2 to 8% by weight), and then the comparison may be made.

[Preparation of Water Absorbent Resin (1)]

In 5500 g of an aqueous solution of sodium acrylate having a neutralization ratio of 75% by mole (monomer concentration: 38% by weight) was dissolved 4.0 g of polyethylene glycol diacrylate (average number of addition mols of ethylene oxide: 9) to give a reaction mixture. Next, the reaction mixture was supplied to a reaction vessel constructed to provide a jacketed stainless double-arm kneader having two sigma-type blades and having an internal volume of 10 L covered by a lid. To the reaction mixture was introduced a nitrogen gas while keeping the reaction mixture at 25° C. to conduct nitrogen gas replacement through removing oxygen dissolved in the reaction mixture. Then, to the reaction mixture were added 28.3 g of a 10% by weight aqueous solution of sodium persulfate and 1.4 g of a 1% by weight aqueous solution of L-ascorbic acid while stirring. One minute thereafter, polymerization was initiated. In 17 minutes following initiation of the polymerization, a polymerization peak temperature of 86° C. was exhibited, and hydrogel polymer was obtained at 35 minutes after initiation of the polymerization. Thus resulting hydrogel polymer had been finely divided into particles of 1 to 4 mm, and the finely divided polymer was spread over a 50 mesh-sized wire mesh (mesh opening: 300 μm), followed by hot-air drying at 160° C. for 60 min. Then, the dried matter was pulverized using a roll mill, and further classified with wire meshes having a mesh opening size of 850 μm and 150 μm. Accordingly, crosslinked polymer powder (a) having an irregular pulverized shape was obtained as a water absorbent resin precursor.

With 100 parts by weight of thus resulting crosslinked polymer powder (a) was mixed by spraying 3.53 parts by weight of an aqueous surface crosslinking agent solution containing 0.5 parts by weight of propylene glycol, 0.03 parts by weight of ethylene glycol diglycidyl ether, 0.3 parts by weight of 1,4-butanediol and 2.7 parts by weight of water. This mixture was subjected to a heat treatment in a mixer at a heat medium temperature of 210° C. for 45 min to obtain a water absorbent resin (1).

[Preparation of Water Absorbent Resin (2)]

In 5500 g of an aqueous solution of sodium acrylate having a neutralization ratio of 75% by mole (monomer concentration: 38% by weight) was dissolved 2.5 g of polyethylene glycol diacrylate (average number of addition mols of ethylene oxide: 9) to give a reaction mixture. Next, the reaction mixture was supplied to a reaction vessel which is the same as that used in preparing the water absorbent resin (1). To the reaction mixture was introduced a nitrogen gas while keeping the reaction mixture at 25° C. to conduct nitrogen gas replacement through removing oxygen dissolved in the reaction mixture. Then, to the reaction mixture were added 28.3 g of a 10% by weight aqueous solution of sodium persulfate and 1.4 g of a 1% by weight aqueous solution of L-ascorbic acid while stirring. Approximately one minute thereafter, polymerization was initiated. In 17 minutes following initiation of the polymerization, a polymerization peak temperature of 86° C. was exhibited, and hydrogel polymer was obtained at 35 minutes after initiation of the polymerization. Thus resulting hydrogel polymer had been finely divided into particles of about 1 to 6 mm. This hydrogel polymer was dried and pulverized in a similar manner as described above, and further classified with wire meshes having a mesh opening size of 850 μm and 150 μl. Accordingly, crosslinked polymer powder (b) having an irregular pulverized shape was obtained as a water absorbent resin precursor.

With 100 parts by weight of thus resulting crosslinked polymer powder (b) was mixed by spraying 3.53 parts by weight of the aqueous surface crosslinking agent solution having the same composition as that described above. This mixture was subjected to a heat treatment in a mixer at a heat medium temperature of 195° C. for 40 min to obtain a water absorbent resin (2).

[Preparation of Water Absorbent Resin (3)]

In 2000 g of an aqueous solution of sodium acrylate having a neutralization ratio of 75% by mole (monomer concentration: 35% by weight) was dissolved 1.7 g of polyethylene glycol diacrylate (average number of addition mols of ethylene oxide: 9) to give a reaction mixture. This reaction mixture was injected into a stainless tray having a size of length: 320 mm, width: 220 mm and height: 50 mm. Depth of the reaction mixture then was 23 mm. Upper part of this stainless tray was sealed with a polyethylene film having a feed port for nitrogen, an exhaust vent and an inlet for charging a polymerization initiator, and placed in a 30° C. water bath. Nitrogen gas was fed to this reaction mixture while keeping the temperature of the reaction mixture to be 30° C., thereby removing oxygen dissolved in the solution. Also in the following period, feeding of nitrogen gas into the upper void space of the reaction vessel was continued while exhausting from the opposite side. Therein were injected 1.6 g of a 10% by weight aqueous solution of 2,2'-azobis(2-amidinopropane)dihydrochloride, 1.6 g of a 10% by weight aqueous solution of sodium persulfate, 2.9 g of a 1% by weight aqueous solution of L-ascorbic acid and 0.3 g of a 3.5% by weight aqueous solution of hydrogen peroxide, followed by mixing sufficiently with a magnetic stirrer. Because polymerization was initiated at one minute after charging the polymerization initiator, the stainless tray was subjected to repeated process of soaking intermittently in a water bath with a liquid temperature of 12° C. such that the tray is soaked into a level corresponding to the height of 10 mm from the bottom of tray to allow for control of the polymerization temperature. In 12 minutes after the initiation of polymerization, the polymerization peak of 74° C. was exhibited. For aging the gel, the tray was soaked in a water bath with a liquid temperature of 60° C. into a level to correspond to the height of 10 mm from the tray bottom, and was kept for 20 min. Thus resulting hydrogel polymer was crushed with a meat chopper equipped with a die having a hole size of 9.5 mm, and was spread over a 50 mesh-sized wire mesh (mesh opening: 300 μm), followed by hot-air drying at 160° C. for 60 min. Then, the dried matter was pulverized using a roll mill, and further classified with wire meshes having a mesh opening size of 850 μm and 150 μm. Accordingly, crosslinked polymer cc) having an irregular pulverized shape was obtained as a water absorbent resin precursor.

With 100 parts by weight of thus resulting crosslinked polymer powder (c) was mixed by spraying 5.03 parts by weight of an aqueous surface crosslinking agent solution containing 1 part by weight of propylene glycol, 0.03 parts by weight of ethylene glycol diglycidyl ether, 1 part by weight of isopropyl alcohol and 3 parts by weight of water. This mixture was subjected to a heat treatment in a mixer at a heat medium temperature of 195° C. for 40 min to obtain a water absorbent resin (3).

[Preparation of Water Absorbent Resin (4)]

In 5500 g of an aqueous solution of sodium acrylate having a neutralization ratio of 75% by mole (monomer concentration: 38% by weight) was dissolved 4.0 g of polyethylene glycol diacrylate (average number of addition mols of ethylene oxide: 9) to give a reaction mixture. Next, the reaction mixture was supplied to a reaction vessel constructed by attaching a lid to a jacketed stainless double-arm kneader having two sigma-type blades and having an internal volume of 10 L. To the reaction mixture was introduced a nitrogen gas while keeping the reaction mixture at 25° C. to conduct nitrogen gas replacement through removing oxygen dissolved in the reaction mixture. Then, to the reaction mixture were added 47.2 g of a 10% by weight aqueous solution of sodium persulfate and 1.4 g of a 1% by weight aqueous solution of L-ascorbic acid while stirring. One minute thereafter, polymerization was initiated. In 15 minutes following initiation of the polymerization, a polymerization peak temperature of 92° C. was exhibited, and hydrogel polymer was obtained at 35 minutes after initiation of the polymerization. Thus resulting hydrogel polymer had been finely divided into particles of 1 to 4 mm. The finely divided hydrogel polymer was spread over a 50 mesh-sized wire mesh (mesh opening: 300 μm), followed by hot-air drying at 160° C. for 60 min. Then, the dried matter was pulverized using a roll mill, and further classified with wire meshes having a mesh opening size of 850 μm and 150 μm. Accordingly, crosslinked polymer powder (d) having an irregular pulverized shape was obtained as a water absorbent resin precursor.

With 100 parts by weight of thus resulting crosslinked polymer powder (d) was mixed by spraying 3.53 parts by weight of an aqueous surface crosslinking agent solution containing 0.5 parts by weight of propylene glycol, 0.03 parts by weight of ethylene glycol diglycidyl ether, 0.3 parts by weight of 1,4-butanediol and 2.7 parts by weight of water. The mixture was subjected to a heat treatment in a mixer at a heat medium temperature of 210° C. for 45 min to obtain a water absorbent resin (4).

Example 1

To 100 parts by weight of the water absorbent resin (1) obtained as described above was added by spraying an aqueous solution containing 5 parts by weight of water and 1 part by weight of sodium hydrogen sulfite (manufactured by Wako Pure Chemical Industries, Ltd., special grade chemical) as a sulfur-containing reducing agent. Addition by spraying was conducted using a hollow cone nozzle 1/4M-K010 (manufactured by Ikeuchi Co., Ltd., droplet diameter: 70 μm to 150 μm). Thus resulting mixture was overlaid to give layers in a thickness of 5 cm, and allowed to stand still and cure in a ventilation type hot-air drier with the atmospheric temperature setting of 80° C. for 30 min. The mixture subjected to the curing treatment was passed through a wire mesh having a mesh opening size of 850 μm to obtain a water absorbing agent (1).

Example 2

To 100 parts by weight of the water absorbent resin (1) was added by spraying an aqueous solution containing 10 parts by weight of water and 1 part by weight of sodium hydrogen sulfite described above. Addition by spraying was conducted using the aforementioned hollow cone nozzle 1/4M-K010 (droplet diameter: 70 μm to 150 μm). Thus resulting mixture was overlaid to give layers in a thickness of 5 cm, and allowed to stand still and cure in a ventilation type hot-air drier with the atmospheric temperature setting of 80° C. for 30 min. The mixture subjected to the curing treatment was passed through a wire mesh having a mesh opening size of 850 μm to obtain a water absorbing agent (2).

Comparative Example 1

The water absorbent resin (1) was directly used as the water absorbing agent for comparison (1) without modification.

Comparative Example 2

To 100 parts by weight of the water absorbent resin (1) was added 1 part by weight of the aforementioned sodium hydrogen sulfite directly in the form of powder, followed by mixing sufficiently to obtain a water absorbing agent for comparison (2).

Example 3

To 100 parts by weight of the water absorbent resin (2) obtained as described above was added by spraying an aqueous solution containing 3 parts by weight of water and 0.5 parts by weight of sodium hydrogen sulfite described above. Addition by spraying was conducted using the aforementioned hollow cone nozzle 1/4M-K010 (droplet diameter: 70 μm to 150 μm). Thus resulting mixture was overlaid to give layers in a thickness of 5 cm, and allowed to stand still and cure in a ventilation type hot-air drier with the atmospheric temperature setting of 80° C. for 30 min. The mixture subjected to the curing treatment was passed through a wire mesh having a mesh opening size of 850 μm to obtain a water absorbing agent (3).

Example 4

To 100 parts by weight of the water absorbent resin (2) was added by spraying an aqueous solution containing 10 parts by weight of water and 1 part by weight of sodium hydrogen sulfite described above. Addition by spraying was conducted using the aforementioned hollow cone nozzle 1/4M-K010 (droplet diameter: 70 μm to 150 μm). Thus resulting mixture was overlaid to give layers in a thickness of 5 cm, and allowed to stand still and cure in a ventilation type hot-air drier with the atmospheric temperature setting of 80° C. for 30 min. The mixture subjected to the curing treatment was passed through a wire mesh having a mesh opening size of 850 μm to obtain a water absorbing agent (4).

Comparative Example 3

The water absorbent resin (2) was directly used as the water absorbing agent for comparison (3) without modification.

Example 5

To 100 parts by weight of the water absorbent resin (3) obtained as described above was added by spraying an aqueous solution containing 5 parts by weight of water and 0.5 parts by weight of sodium hydrogen sulfite described above. Addition by spraying was conducted using the aforementioned hollow cone nozzle 1/4M-K010 (droplet diameter: 70 µm to 150 µm). Thus resulting mixture was overlaid to give layers in a thickness of 5 cm, and allowed to stand still and cure in a ventilation type hot-air drier with the atmospheric temperature setting of 80° C. for 30 min. The cured mixture was passed through a wire mesh having a mesh opening size of 850 µm to obtain a water absorbing agent (5).

Comparative Example 4

The water absorbent resin (3) was directly used as the water absorbing agent for comparison (4) without modification.

Example 6

When the aqueous solution containing 5 parts by weight of water and 0.5 parts by weight of sodium hydrogen sulfite was mixed in Example 5, a straight tube having an internal diameter of 1 mm was used in place of the hollow cone nozzle. Thus, the aqueous solution was mixed by adding, with the droplet diameter of about 2 mm. Thereafter, the same treatment as in Example 5 was carried out to obtain a water absorbing agent (6).

Comparative Example 5

The water absorbent resin (4) obtained as described above was directly used as the water absorbing agent for comparison (5) without modification.

[Preparation of Water Absorbing Agent (7) According to Example 7]

In 2000 g of an aqueous solution of sodium acrylate having a neutralization ratio of 75% by mole (monomer concentration: 39% by weight) was dissolved 2.3 g of polyethylene glycol acrylate (average number of addition mols of ethylene oxide: 9) to give a reaction mixture. Thus resulting reaction mixture was injected into a stainless tray having a size of length: 320 mm, width: 220 mm and height: 50 mm. Thickness of the reaction mixture then was 23 mm. Upper part of the stainless tray was sealed with a polyethylene film having a feed port for nitrogen, an exhaust vent and an inlet for charging a polymerization initiator, and placed in a 25° C. water bath. Nitrogen gas was fed to the reaction mixture while keeping the temperature of the reaction mixture to be 25° C., thereby removing oxygen dissolved in the solution. In the following period, feeding of nitrogen gas into the upper void space of the reaction vessel was continued while exhausting from the opposite side. Therein were injected 8.0 g of a 10% by weight aqueous solution of sodium persulfate as a polymerization initiator and 1.4 g of a 1% by weight aqueous solution of L-ascorbic acid, followed by mixing sufficiently with a magnetic stirrer. Because polymerization was initiated at two minutes after charging the polymerization initiator, the stainless tray was subjected to repeated process of soaking intermittently in a water bath with a liquid temperature of 12° C. such that the tray is soaked into a level corresponding to the height of 10 mm from the bottom of the tray to allow for control of the polymerization temperature. In 15 minutes after the initiation of polymerization, the polymerization peak of 85° C. was exhibited. For aging the gel, the tray was soaked in a water bath with a liquid temperature of 60° C. into a level corresponding to the height from the bottom of the tray of 10 mm, and was kept for 20 min. Thus resulting hydrogel polymer was crushed with a meat chopper (manufactured by Hiraga Seisakusho Co., Ltd., No. 32 meat chopper) equipped with a die having a hole size of 9.5 mm to obtain a particulate hydrogel polymer (polymer gel). Furthermore, this hydrogel polymer (polymer gel) was spread over a 50 mesh-sized wire mesh (mesh opening: 300 µm), followed by hot-air drying at 180° C. for 30 min using an airflow ventilation type batch-wise dryer (manufactured by Stake Chemical Equipment Mfg., Ltd., "type 71-S6"). Next, the dried matter was subjected to a gel pulverizing step in which the dried matter is pulverized with a roll mill, and the pulverized matter was classified with wire meshes having a mesh opening size of 850 µm and 150 µm to obtain crosslinked polymer powder (e) having a particle size of 150 µm to 850 µm and having an irregular pulverized shape, and crosslinked polymer powder (f) having a particle size of smaller than 150 µm.

By repeating the operation described above, 300 g of crosslinked polymer powder (f) was obtained. Thus resulting 300 g of crosslinked polymer powder (f) was charged into a 5 L mortar mixer (manufactured by NISHI NIPPON SHIKENKI: KK) incubated in a water bath at 80° C., and thereto was charged at once an aqueous fluid (s1) for agglomeration of fine particles, which had been kept at 80° C., while stirring with the agitation blade of the mortar mixer at a high velocity of 60 Hz/100 V. The charged aqueous fluid (s1) was an aqueous fluid produced by dissolving 0.08 g of sodium persulfate in 450 g of water at 80° C., which was used immediately after the dissolution. Within 10 seconds after charging, crosslinked polymer powder (f) in fine powdery form was mixed with the aqueous fluid to give agglomerates. Obtaining at 10 minutes after charging the aqueous fluid yielded agglomerated gel having a particle size of 3 to 10 mm. Furthermore, 200 g of thus resulting agglomerated gel and 1800 g of hydrogel polymer (polymer gel) in particulate form obtained by repeating the aforementioned polymerizing step and the aforementioned gel pulverizing step were brought into a slightly stirred state, and the mixture was spread over a 50 mesh-sized wire mesh (mesh opening: 300 µm), followed by hot-air drying at 180° C. for 30 min using an airflow ventilation type batch-wise dryer (manufactured by Satake Chemical Equipment Mfg., Ltd., "type 71-S6") to obtain a dried matter. This dried matter was pulverized with a roll mill, and the pulverized matter was further classified with wire meshes having a mesh opening size of 850 µm and 150 µm to obtain crosslinked polymer powder (g) having a particle size of 150 µm to 850 µm and having an irregular pulverized shape.

With 100 parts by weight of thus resulting crosslinked polymer powder (g) were mixed by spraying 3.5 parts by weight of an aqueous surface crosslinking agent solution containing 0.3 parts by weight of 1,4-butanediol and 0.2 parts by weight of 3-ethyl-3-hydroxymethyloxetane and 3 parts by weight of water. This mixture was subjected to a heat treatment in a mixer at a heat medium temperature of 210° C. for 40 min to obtain a water absorbent resin (7) according to Example 7.

Comparative Example 6

Similarly to the crosslinked polymer powder (g), crosslinked polymer powder (h) having a particle size of 150 µm to 850 µm and having an irregular pulverized shape was obtained except that 450 g of water at 80° C. was used in place of the aqueous fluid (s1) used in the fine particle agglomerating step. With 100 parts by weight of thus resulting crosslinked polymer powder (h) were mixed by spraying 3.5 parts by weight of an aqueous surface crosslinking agent solution containing 0.3 parts by weight of 1,4-butanediol and 0.2 parts by weight of 3-ethyl-3-hydroxymethyloxetane and 3 parts by weight of water. This mixture was subjected to a heat treatment in a mixer at a heat medium temperature of 210° C. for 40 min to obtain a water absorbing agent for comparison (6).

Comparative Example 7

To 100 parts by weight of the crosslinked polymer powder (h) was added an aqueous fluid (s2) containing 0.3 parts by weight of sodium hydrogen sulfite (manufactured by Wako Pure Chemical Industries, Ltd., special grade chemical) and 5 parts by weight of water, followed by mixing. Furthermore, to 100 parts by weight of thus resulting mixture were mixed by spraying 3.5 parts by weight of an aqueous surface crosslinking agent solution containing 0.3 parts by weight of 1,4-butanediol and 0.2 parts by weight of 3-ethyl-3-hydroxymethyloxetane and 3 parts by weight of water. This mixture was subjected to a heat treatment in a mixer at a heat medium temperature of 210° C. for 40 min to obtain a water absorbing agent for comparison (7) according to Comparative Example 7.

Comparative Example 8

To 100 parts by weight of the water absorbing agent for comparison (6) obtained in Comparative Example 6 was added an aqueous fluid (s3) containing 0.05 parts by weight of sodium hydrogen sulfite (manufactured by Wako Pure Chemical Industries, Ltd., special grade chemical) and 30 parts by weight of water, followed by mixing. Moreover, thus resulting mixture was dried at 70° C. for 2 hrs using an airflow ventilation type batch-wise dryer (manufactured by Satake Chemical Equipment Mfg., Ltd., "type 71-S6"). Because the resultant dried matter aggregated rigidly, it could not be passed through a wire mesh having a mesh opening size of 850 µm by the same operation as in Example 1. Thus, the dried matter was pulverized again using a roll mill, and was thereafter passed through a wire mesh having a mesh opening size of 850 µm to obtain a water absorbing agent for comparison (8).

Amount of residual monomer, residual monomer index, absorption capacity without load, absorption capacity under a load of 4.8 kPa, single-layer absorption capacity under a load of 1.9 kPa, percent by weight of particles having a particle size of smaller than 150 µm, brightness by Hunter, and moisture content were measured on each water absorbing agent obtained as described in the foregoings, according to the measurement method described below. The measurement was conducted under conditions of at 25° C.±2° C., and at relative humidity of 50% RH. Also, as the physiological saline solution, a 0.90% by weight aqueous sodium chloride solution was used.

[Amount of Residual Monomer (ppm)]

The water absorbing agent in an amount of 0.500 g was dispersed in 1000 ml of deionized water, and stirred for 2 hrs by a magnetic stirrer having a length of 50 mm to extract the residual monomer. Thereafter, the swollen gel was filtrated using filter paper (manufactured by Toyo Roshi Kaisha Ltd., No. 2, retained particle size specified by JIS P 3801: 5 µm). This filtrate was further subjected to filtration with a filter chromatodisc 25A for pretreatment of HPLC sample (manufactured by Kurabo Industries Ltd., for aqueous system, pore size: 0.45 µm) to prepare a sample for measuring residual monomer. This sample for measuring residual monomer was analyzed on high performance liquid chromatography (HPLC). A calibration curve obtained by analyzing a monomer standard solution presenting known concentration was used as an external standard. Taking into consideration of dilution rate of the water absorbing agent in deionized water, the amount of residual monomer of the water absorbing agent was quantitatively determined. Conditions for measurement on HPLC are as follows.

Carrier solution: aqueous phosphoric acid solution prepared by diluting 3 ml of phosphoric acid (85% by weight, manufactured by Wako Pure Chemical Industries, Ltd., special grade chemical) in 1000 ml of ultra pure water (specific resistance: not less than 15 MΩ·cm)

Carrier speed: 0.7 ml/min.

Column: SHODEX RSpak DM-614 (manufactured by Showa Denko K.K.)

Column temperature: 23±2° C.

Wavelength: UV 205 nm

[Absorption Capacity without Load (CRC) for a Physiological Saline Solution]

A water absorbing agent of 0.20 g was uniformly put in a bag (60 mm×85 mm) made of unwoven fabric and immersed in a physiological saline solution controlled at 25±2° C. The bag was taken out of the solution 30 minutes later, subjected to dewatering for 3 minutes at 250 G (250×9.81 m/sec$^2$) using a centrifuge (Model H-122 small size centrifuge, manufactured by Kokusan Corporation), and then weighed to determine weight W2 (g) of the bag. Weight W1 (g) of the bag was measured after conducting similar operation without using any water absorbing agent. Absorption Capacity (g/g) was then calculated from the weights W1 and W2 according to the following formula.

$$CRC\ (g/g)=(W2-W1)/W0-1$$

wherein, W0 represents weight of the water absorbing agent.

[Absorption Capacity Under a High Load of 4.8 kPa for a Physiological Saline Solution (AAP 4.8 kPa: Absorbency Against Pressure)]

A water absorbing agent of 0.900 g was uniformly scattered on a 400-Mesh wire mesh made of stainless steel (mesh size: 38 µm) welded to the end face (bottom) of a plastic support cylinder having an inner diameter of 60 mm. A piston, which has an outer diameter a little smaller than 60 mm, and which forms no gap against the inner surface of the support cylinder and can move slidably up and down, was mounted on the water absorbing agent. Weight W3 (g) of the support cylinder, the water absorbing agent and the piston was measured. A weight adjusted to be able to press the water absorbing agent uniformly at 4.8 kPa including the weight of the piston was mounted on the piston, thereby completing a set of measuring apparatus. A glass filter having a diameter of 90 mm and a thickness of 5 mm was placed in a Petri dish with a diameter of 150 mm, and thereto was poured a physiological saline solution controlled at 25±2° C. up to the same level as the upper face of the glass filter. A sheet of filter paper with a diameter of 9 cm (No. 2 from Toyo Roshi Kaisha Ltd.) was placed on the surface of the glass filter to be entirely wetted, and excess solution over the wetted filter paper was removed.

The measuring apparatus was placed on the filter paper and the liquid was absorbed with the water absorbing agent under the load. The liquid level was kept constant by adding the liquid when the liquid surface became lower than the upper face of the glass filter. The measuring apparatus was taken out after an hour and weight W4 (g) (weight of the support cylinder, the swollen water absorbing agent and the piston)

excluding the used weight was measured again. The absorption capacity under a high load of 4.8 kPa (g/g) was calculated from the weights W3 and W4 according to the following formula.

$$AAP\ 4.8\ kPa\ (g/g)=(W4-W3)/W0$$

wherein, W0 represents weight of the water absorbing agent.

[Single-Layer Absorption Capacity Under a Load of 1.9 kPa for a Physiological Saline Solution (SAAP; Single-Layer AAP 1.9 kPa: Single-Layer Absorbency Against Pressure)]

Measurement was conducted similarly to the aforementioned absorption capacity under a high load of 4.8 kPa except that the weight of the water absorbing agent was changed from 0.900 g to 0.200 g and that a weight which was adjusted to be able to press the water absorbing agent uniformly at 1.9 kPa including the weight of the piston was mounted. Single-layer absorption capacity (g/g) under a load of 1.9 kPa was calculated according to the following formula.

$$SAAP\ (g/g)=(W6-W5)/W0$$

(wherein W5 represents weight of the support cylinder, water absorbing agent before water absorption and piston; W6 represents weight of the support cylinder, water absorbing agent after water absorption and piston; and W0 represents weight of the water absorbing agent).

[Percent by Weight of Particles Having a Particle Size of Smaller than 150 μm]

The water absorbing agent was subjected to sieve classification using JIS standard sieves having mesh opening size of 850 μm, 710 μm, 600 μm, 500 μm, 425 μm, 300 μm, 212 μm, 150 μm, 106 μm and 45 μm, and a tray, and then percent by weight of particles having a particle size of smaller than 150 μm was determined by actual measurement. Furthermore, with respect to each range of particle size distribution, percentages R were plotted on a logarithmic probability paper. Particle size corresponding to R=50% by weight was thus determined as mass median particle size (D50). In addition, logarithmic standard deviation (σζ) is represented by the following formula, wherein smaller value of σζ means narrower particle-size distribution.

$$\sigma\zeta=0.5\times\ln(X2/X1)$$

wherein, X1 and X2 represent particle size for R=84.1% by weight and for R=15.9% by weight, respectively.

For sieve classification, the water absorbing agent of 10.00 g was charged into a set of the JIS standard mesh sieves having each mesh opening size (The IIDA TESTING SIEVE: inner diameter of 80 mm) and sieved shaking for 5 minutes using a Ro-tap sieve shaker (Model ES-65 sieve shaker from Iida Seisakusho Co., Ltd.).

[Brightness by Hunter (WB)]

Brightness by Hunter was measured using Hunter colorimeter. Greater value of the brightness by Hunter indicates that brightness is higher.

[Moisture Content (H) of Water Absorbing Agent]

The water absorbing agent of 2.000 g was accurately weighed in an aluminum cup having a diameter of the bottom face of approximately 50 mm, and then total weight W7 (g) of the water absorbing agent and the aluminum cup was measured. Subsequently, it was dried by allowing to stand still in an oven with the atmospheric temperature of 180° C. for 3 hrs. Three hours later, the aluminum cup and the water absorbing agent removed from the oven were sufficiently cooled to room temperature in a desiccator. Total weight W8 (g) of the water absorbing agent and the aluminum cup after drying was measured, and the moisture content was determined according to the following formula.

$$H(\%\ by\ weight)=(W7-W8)/W0$$

wherein, W0 represents weight of the water absorbing agent.

[Content (ppm) of Sulfur Based Volatile Component of Water Absorbing Agent]

The water absorbing agent obtained in each of Examples and Comparative Examples in an amount of 6.00 g was uniformly spread in a glass Petri dish (Code: 305-07, external diameter: 120 mm×height: 25 mm, described in GENERAL CATALOGUE A-1000 (published in 2003) published by SOGO LABORATORY GLASS WORKS CO., LTD). Then, the water absorbing agent was covered by a sheet of breathable and liquid permeable heatlon paper (Nangoku Pulp Technical Corporation, type: GSP-22) cut into circular (diameter: 116 mm). Nonwoven fabric can be used in place of heatlon paper. Outer circumference of the heatlon paper or nonwoven fabric was fixed on inner wall of the glass Petri dish with a tape (10 mm×10 mm) at three sites. One edge of a 3 L sniffing bag (manufactured by OMI ODORAIR SERVICE Corporation) was opened, and after placing the glass Petri dish including the spread water absorbing resin therein, and opened part of the sniffing bag was closed with an adhesive tape not to leave any space. After depressurizing inside of the sniffing bag once from a glass tube attached to the sniffing bag, odorless air of 1.2 L was fed therein, and subsequently, 30 ml of a 0.90% by weight aqueous solution of sodium chloride (physiological saline solution) adjusted to a temperature of 25±2° C. was poured at once to the dish in the sniffing bag, while preventing contamination of the ambient air, using a glass funnel connected to a Teflon (registered trade name) tube. Then, the water absorbing agent was allowed to be uniformly swollen, and the bag was sealed hermetically with a silicon rubber stopper. The bag was left to stand in an incubator at 37° C. to permit swelling. The bag was recovered 60 minutes later, which was left to stand at room temperature. After leaving to stand at room temperature for 10 minutes, the silicon rubber stopper was removed, and atmospheric concentration was measured using a gas sampler (manufactured by Gastec Corporation, GV-100S) and a gas detector tube (manufactured by Gastec Corporation, No. 5Lb, subject gas for measurement: sulfur dioxidize) while preventing contamination of the ambient air. This atmospheric concentration was defined as content (ppm) of the sulfur based volatile component volatilized from the water absorbing agent.

In the measurement method, as the case may be, the gas detector tube may execute detection to result in change of color even though similar operation is conducted using a physiological saline solution alone without using a water absorbing agent. In such a case, correction was performed by subtracting a blank value detected in the indicator range yielded when a physiological saline solution alone was used (detection limit: 0.05 ppm).

Results of measurement on the physical properties described above are shown in the following Table 1 and Table 2.

[Sensory Test of Odor]

Sensory evaluation was made on the water absorbing agents (1) to (7) and water absorbing agents for comparison (1) to (8), respectively. The water absorbing agent in an amount of 1 part by weight was swollen in 20 parts by weight of a 0.9% by weight physiological saline solution, and hermetically left to stand at 37° C. for 1 hour. Thereafter, sensory test of odor by 10 adult subjects was carried out. In the evaluation method, those not having an unpleasant odor were scored 0 point; those having an unpleasant odor were scored 5 points; and accordingly, evaluation on the grade of 5 scale was made depending on degree of the unpleasantness experienced by the subject. Average score from 10 subjects corresponds to the odor point. As this odor point is lower, generation of less unpleasant odor is indicated. Results of this odor point are shown in the following Table 1 and Table 2. As a control standard for comparison, the water absorbent resin (1) was used. Thus, evaluation was made using the odor point of this water absorbent resin (1) assumed to be 3.0.

As is seen from the results of the sensory test of odor, the water absorbing agent for comparison (2) prepared by directly mixing sodium hydrogen sulfite in the state of powder as a sulfur-containing reducing agent exhibited an odor specific for sodium hydrogen sulfite, whereby resulting in increase of unpleasantness experienced by the subject. Moreover, even if the sodium hydrogen sulfite was added in the state of an aqueous solution, unpleasantness experienced by the subject was ascertained to be increased when a heat treatment at high temperature (for example, 210° C. with regard to Comparative Example 7) was carried out in the following step. In contrast, it was revealed that the unpleasantness experienced by the subject is decreased when the method in which the residual monomer is reduced in the fine powder agglomerating step as in Example 7, or a method in which a sulfur-containing reducing agent is added to the water absorbent resin after the surface crosslinking following completing the high temperature treatment is employed.

[Evaluation of Absorbent Core (Evaluation of Variance of the Amount of Residual Monomer)]

A water-absorbent core including 10 g of a water absorbing agent and 10 g of fluff pulp was produced using the water absorbing agent (3) obtained in Example 3 and fluff pulp as a hydrophilic fiber. Details of the method for the production of this water-absorbent core will be described below. The water absorbing agent (3) in an amount of 100 parts by weight was charged in a hopper, and setting was executed so that the water absorbing agent was dropped on the wire mesh intermittently, in response to on-off switching of the vibrating feeder, the conveyed and charged amount of which had been adjusted beforehand. On the other hand, setting was executed such that the fluff pulp was dropped on the wire mesh in a predetermined amount while being disentangled in a time period starting from time point before the dropping of the water absorbing agent (3) over the time point when the dropping of the water absorbing agent (3) in a predetermined amount was terminated. The water-absorbent core is produced by dropping the water absorbing agent (3) and the fluff pulp on a wire mesh that has a frame (length: 12 cm, width: 12 cm) and has a mesh opening size of 150 μm, and aspirating them from the bottom side of the wire mesh. First, supply of the fluff pulp was started, and then the switch of the vibrating feeder that supplies the water absorbing agent (3) was turned on to drop the water absorbing agent (3) in a predetermined amount for a predetermined time period after formation of the fluff pulp layer was initiated on the wire mesh. Accordingly, the water-absorbent core was produced. Through repeating this operation, 10 sheets of the water-absorbent cores (1) to (10) were produced. Each of the resulting water-absorbent cores (1) to (10) was placed in a polyethylene bag (length: 20 cm, width: 24 cm). After sealing the opening of the bag, the bag was shaken. Separation of the water absorbing agent (3) from the fluff pulp yielded separated water absorbing agents (3)-1 to (3)-10. Residual monomer of the resulting each water absorbing agent is shown in Table 3.

Moreover, through carrying out similar operation using the water absorbing agent for comparison (5) obtained in Comparative Example 5, the water absorbing agents for comparison (5)-1 to (5)-10 were obtained. Residual monomer of the resulting each water absorbing agent is shown in Table 3 below.

TABLE 1

Specification and Evaluation Results of Examples

|  | Example 1 | Example 2 | Example 3 | Example 4 | Example 5 | Example 6 | Example 7 |
|---|---|---|---|---|---|---|---|
| Water absorbing agent | water absorbing agent (1) | water absorbing agent (2) | water absorbing agent (3) | water absorbing agent (4) | water absorbing agent (5) | water absorbing agent (6) | water absorbing agent (7) |
| Amount of residual monomer (ppm) | 258 | 106 | 269 | 86 | 288 | 331 | 281 |
| Weight ratio of particles having particle size of 300-850 μm to particles having particle size of smaller than 300 μm | 79/21 | 83/17 | 74/26 | 84/16 | 76/24 | 68/32 | 72/28 |
| Amount of residual monomer of particles having particle size of 300-850 μm (ppm) | 301 | 108 | 285 | 84 | 287 | 338 | 259 |
| Amount of residual monomer of particles having particle size of smaller than 300 μm (ppm) | 233 | 81 | 266 | 71 | 280 | 357 | 332 |
| Residual monomer index | 0.26 | 0.25 | 0.07 | 0.15 | 0.02 | 0.06 | 0.26 |
| Absorption capacity without load (g/g) | 34 | 32 | 42 | 39 | 34 | 34 | 31 |
| Absorption capacity under a high load of 4.8 kPa (g/g) | 24 | 22 | 15 | 14 | 26 | 25 | 25 |
| Single-layer absorption capacity under a load of 1.9 kPa (g/g) | 30 | 29 | 34 | 31 | 34 | 33 | 29 |
| Proportion of particles having particle size of smaller than 150 μm (%) | 1.5 | 0.6 | 1.0 | 0.8 | 1.0 | 1.3 | 0.8 |
| Brightness by Hunter | 72 | 72 | 71 | 71 | 74 | 74 | 70 |
| Moisture content (%) | 4.0 | 8.2 | 2.2 | 7.8 | 4.5 | 4.2 | 0.3 |

TABLE 1-continued

Specification and Evaluation Results of Examples

|  | Example 1 | Example 2 | Example 3 | Example 4 | Example 5 | Example 6 | Example 7 |
|---|---|---|---|---|---|---|---|
| Content of sulfur based volatile component (ppm) | 0.1 | 0 | 0 | 0 | 0 | 0 | 0 |
| Results of sensory test (Odor point) | 3.1 | 3.2 | 2.9 | 3.3 | 3.0 | 2.9 | 3.1 |

TABLE 2

Specification and Evaluation Results of Comparative Examples

|  | Comp. Example 1 | Comp. Example 2 | Comp. Example 3 | Comp. Example 4 | Comp. Example 5 | Comp. Example 6 | Comp. Example 7 | Comp. Example 8 |
|---|---|---|---|---|---|---|---|---|
| water absorbing agent | for comparison (1) | for comparison (2) | for comparison (3) | for comparison (4) | for comparison (5) | for comparison (6) | for comparison (7) | for comparison (8) |
| Amount of residual monomer (ppm) | 353 | 350 | 306 | 470 | 268 | 540 | 435 | 93 |
| Weight ratio of particles having particle size of 300-850 μm to particles having particle size of smaller than 300 μm | 67/33 | 66/34 | 67/33 | 66/34 | 66/34 | 72/28 | 72/28 | 69/31 |
| Amount of residual monomer of particles having particle size of 300-850 μm (ppm) | 342 | 320 | 298 | 455 | 260 | 497 | 422 | 76 |
| Amount of residual monomer of particles having particle size of smaller than 300 μm (ppm) | 468 | 428 | 406 | 623 | 355 | 751 | 568 | 108 |
| Residual monomer index | 0.36 | 0.31 | 0.35 | 0.36 | 0.35 | 0.47 | 0.35 | 0.34 |
| Absorption capacity without load (g/g) | 36 | 36 | 43 | 36 | 36 | 31 | 30 | 22 |
| Absorption capacity under a high load of 4.8 kPa (g/g) | 25 | 24 | 16 | 28 | 19 | 25 | 25 | 16 |
| Single-layer absorption capacity under a load of 1.9 kPa (g/g) | 32 | 32 | 35 | 35 | 28 | 29 | 28 | 20 |
| Proportion of particles having particle size of smaller than 150 μm (%) | 1.8 | 1.9 | 1.5 | 1.8 | 1.4 | 0.8 | 0.8 | 1.6 |
| Brightness by Hunter | 72 | 72 | 71 | 74 | 68 | 70 | 70 | 71 |
| Moisture content (%) | 0.3 | 0.3 | 0.3 | 0.3 | 0.3 | 0.3 | 0.3 | 26 |
| Content of sulfur based volatile component (ppm) | 0 | 3.0 | 0 | 0 | 0 | 0 | 0 | 0 |
| Results of sensory test (Odor point) | 3.0 | 4.1 | 3.2 | 3.0 | 3.5 | 3.1 | 4.8 | 3.8 |

TABLE 3

Evaluation of variance of amount of residual monomer

| Water absorbing agent | Residual monomer (ppm) |
|---|---|
| Water absorbing agent (3)-1 | 268 |
| Water absorbing agent (3)-2 | 271 |
| Water absorbing agent (3)-3 | 295 |
| Water absorbing agent (3)-4 | 265 |
| Water absorbing agent (3)-5 | 248 |
| Water absorbing agent (3)-6 | 283 |
| Water absorbing agent (3)-7 | 268 |
| Water absorbing agent (3)-8 | 270 |
| Water absorbing agent (3)-9 | 240 |
| Water absorbing agent (3)-10 | 276 |
| Average | 268 |
| Standard deviation | 16 |
| Water absorbing agent for comparison (5)-1 | 222 |
| Water absorbing agent for comparison (5)-2 | 235 |
| Water absorbing agent for comparison (5)-3 | 260 |
| Water absorbing agent for comparison (5)-4 | 252 |
| Water absorbing agent for comparison (5)-5 | 246 |
| Water absorbing agent for comparison (5)-6 | 260 |
| Water absorbing agent for comparison (5)-7 | 281 |
| Water absorbing agent for comparison (5)-8 | 338 |
| Water absorbing agent for comparison (5)-9 | 321 |
| Water absorbing agent for comparison (5)-10 | 344 |
| Average | 276 |
| Standard deviation | 44 |

In Table 1 and Table 2, comparison of Examples 1 and 2 with Comparative Example 1, comparison of Examples 3 and 4 with Comparative Example 3 revealed that the water absorbing agents of Examples 1 to 4 included low amount of residual monomer, exhibited small variance of the amount of residual monomer among ranges of particle size distribution, and was sanitary. Moreover, comparison of Example 2 with Comparative Example 2, and comparison of Example 5 with Example 6 revealed that for obtaining a water absorbing agent having the physical properties as described above, not only merely mixing the sulfur-containing reducing agent with the water absorbent resin, but also homogenously mixing the aqueous sulfur-containing reducing agent solution with the water absorbent resin is effective. Furthermore, although lowering of the amount of residual monomer was contemplated through increasing the amount of the polymerization initiator in Comparative Example 5, it was elucidated that the residual monomer index could not be reduced in the range according to other Examples, and in addition, lowering of the brightness by Hunter as well as lowering of absorption capacity under a high load of 4.8 kPa were found.

Comparison of Example 7 with Comparative Example 6 revealed that when the amount of residual monomer retained by fine particles was reduced in the step for obtaining agglomerated gel of fine powder, the amount of residual monomer of the resulting water absorbing agent is reduced, and the residual monomer index can be also reduced. Moreover, also taking into consideration of Comparative Example 5, it can be concluded that lowering of the residual monomer through selecting the method of Example 7 is more efficient, and the residual monomer index can be also reduced than in the case of increasing the amount of polymerization initiator in polymerization.

Still further, as is clear from comparison of Example 7 with Comparative Example 8, the residual monomer could be reduced enough according to the method of Comparative Example 8, while the residual monomer index falling within the desired range could not be attained. In addition, because the moisture content was high and thus proportion of the Water absorbent resin component in the water absorbing agent (solid content) was lowered in Comparative Example 8, the absorption capacity without load and the absorption capacity under a high load became low. Moreover, in Comparative Example 8, pulverizing step was, carried out again after the surface crosslinking treatment for the purpose of pulverizing rigid agglomerates, however, it was proven that this operation resulted in destruction of the surface-crosslinked layer, thereby reducing the absorption capacity under a load to a greater extent than the lowering which may be caused by the lowered solid content.

As is shown in Table 1 and Table 2, Example 3 and Comparative Example 5 exhibited approximately the same amount of residual monomer. However, as is clear from Table 3, variance on each water-absorbent core was smaller in Example 3 which could achieve low residual monomer index, in comparison with Comparative Example 5 although the amount of residual monomer was approximately the same in both cases.

As described hereinabove, according to the method for the production of the water absorbing agent of the present invention, a water absorbing agent having a low amount of residual monomer, and small variance of the amount of residual monomer among ranges of particle size distribution can be obtained. This water absorbing agent is not colored, does not emit any bad smell, and has well-balanced favorable physical properties, without causing a problem of impairment of physical properties due to deterioration of the polymer.

Moreover, the water absorbing agent of the present invention exhibits favorable physical properties, low amount of residual monomer, and small variance of the amount of residual monomer among ranges of particle size distribution, therefore, when it is used in absorbing articles such as diapers, variance among the products may be lessened, and sanitary products can be provided even in the cases in which it is used in absorbing articles of slim type.

INDUSTRIAL APPLICABILITY

The water absorbing agent of the present invention can be applied to uses requiring water absorbing capacity and water retaining capacity including water absorbing agents for sanitary goods such as diapers and sanitary napkins, water retaining agents for medical use, water retaining agents for agricultural and horticultural use, and dehydrating agents for other industrial use, and the like.

The foregoing explanations are for merely showing an example, and various modifications can be made without departing from the principles of the present invention.

The invention claimed is:

1. A particulate water absorbing agent comprising a water absorbent resin as a principal component,
   wherein the absorbent resin has a cross-linked structure including a constitutional unit derived from an unsaturated carboxylic acid and/or a salt thereof and is obtained by a surface crosslinking treatment around the surface thereof with a surface crosslinking agent,
   said water absorbing agent comprising particles having a particle size of 300 to 850 µm and particles having a particle size of smaller than 300 µm,
   wherein the amount of residual monomer is not lower than 0 but not higher than 500 ppm, and
   residual monomer index (RMI) calculated by the following formula (1):

$$RMI=|RM_1-RM_2|/RM_A \quad (1)$$

wherein, $RM_1$ represents the amount of residual monomer of the water absorbing agent having a particle size of smaller than 300 µm among the particles constituting the water absorbing agent; $RM_2$ represents the amount of residual monomer of the water absorbing agent having a particle size of 300 to 850 µm among the particles constituting the water absorbing agent; and $RM_A$ represents the amount of residual monomer of the water absorbing agent,
   is not greater than 0.30.

2. The water absorbing agent according to claim 1 wherein the amount of residual monomer is not lower than 0 but not higher than 300 ppm.

3. The water absorbing agent according to claim 1 wherein main component of said unsaturated carboxylic acid is acrylic acid, and said residual monomer is acrylic acid and/or a salt thereof.

4. The water absorbing agent according to claim 1 wherein weight ratio of particles having a particle size of 300 to 850 µm to particles having a particle size of smaller than 300 µm is not less than 20/80 but not greater than 80/20.

5. The water absorbing agent according to claim 1 wherein absorption capacity without load (CRC) for a physiological saline solution is not less than 30 g/g, and absorption capacity under a high load of 4.8 kPa (AAP 4.8 kPa) for a physiological saline solution is not less than 20 g/g.

6. The water absorbing agent according to claim 1 wherein total absorption capacity (TAC) for a physiological saline solution which is calculated by the following formula (2):

$$TAC\ (g/g)=CRC+SAAP \quad (2)$$

wherein, CRC represents absorption capacity without load (g/g), and SAAP (Single-layer AAP) represents single-layer absorption capacity under a load of 1.9 kPa (g/g),
   is not less than 65 g/g.

7. The water absorbing agent according to claim 1 wherein content of the particles having a particle size of smaller than 150 μm is not higher than 2% by weight.

8. The water absorbing agent according to claim 1 wherein the particle has an irregular pulverized shape.

9. The water absorbing agent according to claim 1 which comprises an oxidizing agent, a reducing agent or a persulfate salt, and a water absorbent resin.

10. The water absorbing agent according to claim 1 which comprises a sulfur-containing reducing agent and a water absorbent resin.

11. A water absorbing agent according to claim 1 wherein the water absorbent resin which has a cross-linked structure including a constitutional unit derived from an unsaturated carboxylic acid and/or a salt thereof and which is obtained by said surface crosslinking treatment around the surface thereof with said surface crosslinking agent; and a sulfur-containing reducing agent,
- wherein absorption capacity without load (CRC) for a physiological saline solution is not less than 32 g/g,
- absorption capacity under a high load of 4.8 kPa (AAP 4.8 kPa) for a physiological saline solution is not less than 20 g/g,
- content of sulfur based volatile component as an atmospheric concentration specified by a gas detector tube is not less than 0 but not higher than 2.5 ppm.

12. An absorbing article which comprises the water absorbing agent according to claim 11.

13. An absorbing article comprising the water absorbing agent of claim 1.

* * * * *